United States Patent
Kuo et al.

[11] Patent Number: 5,929,236
[45] Date of Patent: Jul. 27, 1999

[54] 2-SUBSTITUTED MORPHOLINE AND THIOMORPHOLINE DERIVATIVES AS GABA-B ANTAGONISTS

[75] Inventors: Shen-Chun Kuo, Union; David J. Blythin, North Caldwell; William Kreutner, West Caldwell, all of N.J.

[73] Assignee: Schering Corporation, Kenilworth, N.J.

[21] Appl. No.: 08/525,795

[22] PCT Filed: Mar. 23, 1994

[86] PCT No.: PCT/US94/02803

§ 371 Date: Sep. 22, 1995

§ 102(e) Date: Sep. 22, 1995

[87] PCT Pub. No.: WO94/22843

PCT Pub. Date: Oct. 13, 1994

Related U.S. Application Data

[63] Continuation-in-part of application No. 08/038,584, Mar. 26, 1993., abandoned

[51] Int. Cl.$^6$ .......... C07D 417/00; C07D 413/00
[52] U.S. Cl. .......... 544/60; 544/56; 544/57; 544/59; 544/111; 544/157; 544/171
[58] Field of Search .......... 544/111, 157, 544/171, 59, 60

[56] References Cited

FOREIGN PATENT DOCUMENTS 311948 10/1988 European Pat. Off. .
398426 5/1990 European Pat. Off. .

OTHER PUBLICATIONS

Abstract to JP 56002976, Jan. 13, 1981.
Abstract to Masuoka et al., "Syntheses of 3,4–dihydro–2H–1,4–benzoxazine–2–acetates and related compounds", Chem. Pharm. Bull., 34(1), pp. 130–139 1986.
Olpe, et al., *Eur. J. Pharmacol.*, 187, 27–38 (1990).
Hills, et al., *Br. J. Pharmacol.*, 102, 5–6 (1991).
Snead III, et al., *Pharmacology Communications*, 2, 63–69 (1992).
Hosford, et al., *Pharmacology Communications*, 2, 123–124 (1992).
Mondadori, et al., *Pharmacology Communications*, 2, 93–97 (1992).
Bowery, et al., *Arzneim.–Forsch./Drug Res.*, 42, No. 2a, 215–223 (1992).
Loftus, *Syn. Comm.*, 10 (1), 59–73 (1980).
Walton, et al., *J. Amer. Chem. Soc.*, 77, 5144 (1955).
Hills, et al., *Br. J. Pharmacol.*, 97, 1292–1296 (1989).
Hosford, et al., *Pharmacology Communications*, 2, 167–168 (1992).
Klebs, et al., *Pharmacology Communications*, 2, 171–172 (1992).
Kerr, et al., in *GABA$_B$Receptors in Mammalian Function*, Bowery, et al., eds., 29–45 (Chichester 1990).
Karlsson, et al., in *GABA$_B$Receptors in Mammalian Function*, Bowery, et al., eds., 349–365 (Chichester 1990).
Chem Abstracts 118: 191749p, 1993.

*Primary Examiner*—Dwayne C. Jones
*Attorney, Agent, or Firm*—Palaiyur S. Kalyanaraman; Anita W. Magatti; John J. Maitner

[57] ABSTRACT

Disclosed are compounds of the formula I

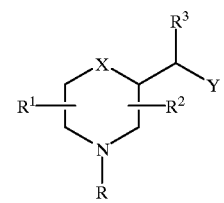

wherein:

Y represents —CO$_2$H, —CO$_2$R$^6$, —C(O)NHR$^7$, —SO$_2$H, —SO$_3$H, —SO$_3$R$^6$, —SO$_2$NHR$^7$, —C(O)—N(OH)—R$^8$, or a group of the formula

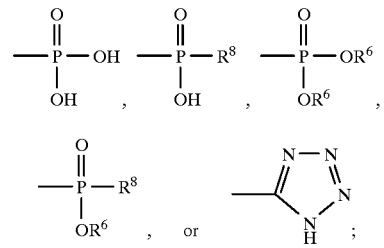

or a pharmaceutically acceptable addition salt or solvate thereof. Also disclosed are pharmaceutical compositions containing compounds of Formula I. Further disclosed is a method for treating or preventing respiratory depression, epileptic seizures or other central nervous system disorders, and for enhancing cognitive performance, by administering an effective amount of a compound of Formula I.

10 Claims, No Drawings

2-SUBSTITUTED MORPHOLINE AND THIOMORPHOLINE DERIVATIVES AS GABA-B ANTAGONISTS

The present application is United States national application corresponding to International Application No. PCT/US 94/02803, filed Mar. 23, 1994 and designating the United States, which PCT application is in turn a continuation-in-part of U.S. application Ser. No. 08/038,584, filed Mar. 26, 1993 abandoned on May 2, 1994 the benefit of which applications are claimed pursuant to the provisions to the 35 U.S.C. 120, 363 and 365 (C).

BACKGROUND OF THE INVENTION

The present invention relates to morpholine and thiomorpholine derivatives, pharmaceutical compositions, and methods of using such derivatives.

It is well established that there are two classes of receptors for the neurotransmitter γ-aminobutyric acid (GABA), which have been identified as $GABA_A$ and $GABA_B$. Selective $GABA_B$ agonists, such as (−)-baclofen, are known and have demonstrated clinical utility as muscle relaxants. Kerr, et al, in *$GABA_B$ Receptors in Mammalian Function*, Bowery, et al, eds., pp. 29–45, (Chichester 1990), have reported low affinity $GABA_B$ antagonists, such as phaclofen and 2-hydroxy saclofen. Olpe, et al, *Eur. J. Pharmacol.*, 187, 27 (1990), discloses the $GABA_B$ antagonist 3-aminopropyl (diethoxymethyl)phosphinic acid (CGP 35348), which, although having a low receptor affinity (comparable to 2-hydroxy saclofen), can penetrate the blood/brain barrier. In addition, Hills, et al, *Br. J. Pharmacol.*, 102, pp. 5–6 (1991) discloses phosphinic acid derivatives having activity as $GABA_B$ antagonists.

General absence (petit mal) seizures are a clinically and experimentally unique class of seizures, typically occuring in children. It has been reported that $GABA_B$ antagonists are effective in blocking the occurrence of petit mal seizures in a number of animal models: Snead III, *Pharmacology Communications*, 2 (1-2), pp. 63–69 (1992); Hosford, et al, *Pharmacology Communications*, 2 (1-2), pp. 123–124 (1992).

Mondadori, et al, *Pharmacoloay Communications*, 2 (1-2), pp. 93–97 (1992), disclose the use of $GABA_B$ receptor antagonists for improving cognitive performance in animal models.

Bowery, et al, *Arzneim. -Forsch./Drug Res.*, 42 (I), Nr. 2a, pp. 215–223 (1992) relates to the physiological role of $GABA_B$ receptor antagonists.

Morpholine and thiomorpholine derivatives bearing substituents at the 2 position are known. Loftus, *Syn. Comm.*, 10 (1), 59–73 (1980), discloses compounds of the formula

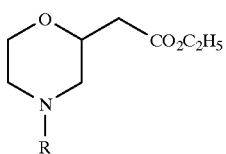

wherein R is methyl or benzyl.

European Patent Publication EP 398426 discloses compounds of the formula

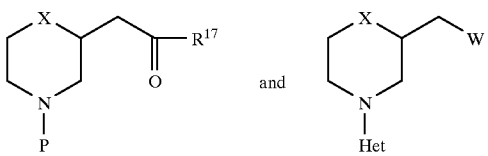

wherein: X is O or S; P is $C_6H_5$—$CH_2$— or $C_6H_5$—$CH_2$—O—C(O)—; $R^{17}$ is $C_1$-$C_4$ alkoxy or OH; W is a reactive leaving group, such as halogen or sulfonyloxy; and Het represents a heteroaryl group.

European Patent Publication EP 311948 discloses compounds of the formula

wherein Z is a Cl, Br, I, —$SO_2CH_3$ or —$SO_2$—$C_6H_4$—$CH_3$.

SUMMARY OF THE INVENTION

Novel compounds of the present invention are represented by the formula I

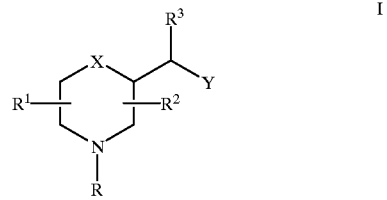

wherein:
X is O or S;
Y represents —$CO_2H$, —$CO_2R^6$, —C(O)$NHR^7$, —$SO_3H$, —$SO_2H$, —$SO_3R^6$, —$SO_2NHR^7$, —C(O)—N(OH)—$R^8$, or a group of the formula

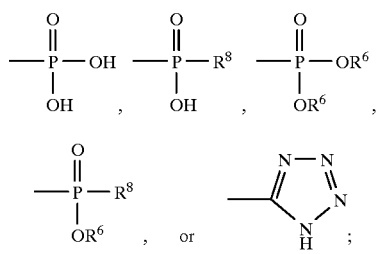

R is selected from the group consisting of H, $C_1$-$C_8$ alkyl, $C_1$-$C_8$ alkanoyl, $C_1$-$C_8$ alkoxycarbonyl, $C_3$-$C_8$ cycloalkyl, $C_3$-$C_8$ cycloalkyl($C_1$-$C_8$)alkyl, Ar—($C_1$-$C_8$)alkyl and Ar—$CH_2$—O—C(O)—;
Ar represents phenyl optionally substituted by 1 to 3 substituents selected from $C_1$-$C_6$ alkyl, halogeno, —CN, —$NO_2$, —$CF_3$, —OH, —$OR^6$ and —$OCF_3$;
$R^1$ and $R^2$ are independently substituents attached at the 2-, 3-, 5- or 6- position of the heterocyclic ring;
$R^1$ is selected from the group consisting of $C_1$-$C_8$ alkyl and hydroxy($C_1$-$C_8$)alkyl; and $R^1$ also represents H where:
(a) R is H and $R^7$ is $C_1$–$C_6$ alkyl or

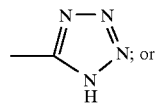; or (b) X is S; or
(c) Y is —$SO_3H$, —$SO_2H$, —$SO_3R^6$, —$SO_2NHR^7$, or a group of the formula

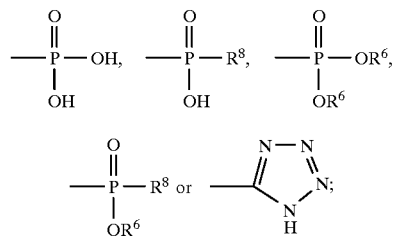

$R^2$ is selected from the group consisting of H, $C_1$–$C_8$ alkyl and hydroxy($C_1$–$C_8$)alkyl; or where $R^1$ and $R^2$ are attached at adjacent positions of the heterocyclic ring: $R^1$ and $R^2$ together with the carbon atoms to which they are attached may also comprise a fused 3–8 membered carbocyclic ring, which ring may be optionally substituted by an —OH group; or where $R^1$ and $R^2$ are attached at the same position of the heterocyclic ring: $R^1$ and $R^2$ together with the carbon atom to which they are attached may also comprise a 3–8 membered carbocyclic spiro ring, which ring may be optionally substituted by an —OH group;

$R^3$ is H, $C_1$–$C_8$ alkyl or hydroxy($C_1$–$C_8$)alkyl;
$R^6$ is $C_1$–$C_6$ alkyl;
$R^7$ is H, $C_1$–$C_6$ alkyl or

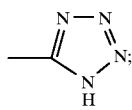

$R^8$ is H, $C_1$–$C_8$ alkyl, $C_3$–$C_8$ cycloalkyl, $C_3$–$C_8$ cycloalkyl ($C_1$–$C_8$)alkyl, Ar or Ar—($C_1$–$C_8$)alkyl;

or a pharmaceutically acceptable addition salt or solvate thereof.

Preferred are compounds of the formula Ia,

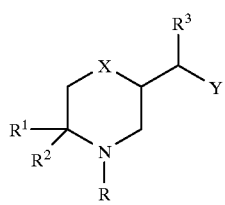

Ia i.e., compounds of the formula I wherein $R^1$ and $R^2$ are both attached at the 5- position of the heterocyclic ring.

Also preferred are compounds of the formula I wherein Y is —$CO_2H$, —$CO_2R^6$, —C(O)$NHR^7$, or —C(O)—N(OH)—$R^8$.

Another group of preferred compounds are compounds of the formula I wherein Y is a group of the formula

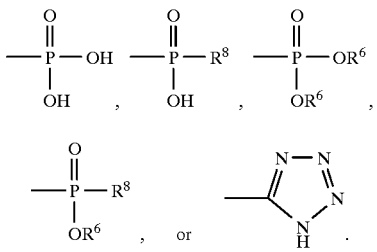

Yet another group of preferred compounds are compounds of formula I wherein R is hydrogen.

Still another group of preferred compounds are compounds of the formula I wherein X is O.

Compounds wherein $R^3$ is H are also preferred.

More preferred are compounds of the formula Ia wherein Y is —$CO_2H$, —$CO_2R^6$, —C(O)$NHR^7$, or —C(O)—N(OH)—$R^8$.

Another group of more preferred compounds are compounds of the formula Ia wherein R is hydrogen.

Yet another group of more preferred compounds are compounds of formula Ia wherein $R^2$ is hydrogen and $R^1$ is —$CH_3$, —$C_2H_5$ or —$CH_2OH$.

Still another group of more preferred compounds are compounds of the formula Ia wherein Y is a group of the formula

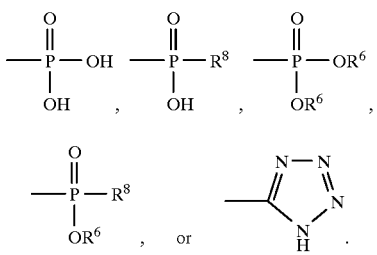

Also more preferred are compounds of the formula Ia wherein $R^1$ and $R^2$ are independently selected from the group consisting of —$CH_3$, —$C_2H_5$ and —$CH_2OH$.

Still another group of more preferred compounds are compounds of the formula Ia wherein $R^1$ and $R^2$, together with the carbon atom to which they are attached, comprise a 3–8 membered carbocyclic spiro ring, which ring is optionally substituted by an —OH group.

Most preferred are compounds of the formula Ia wherein R and $R^3$ are both hydrogen and Y is —$CO_2H$ or a group of the formula

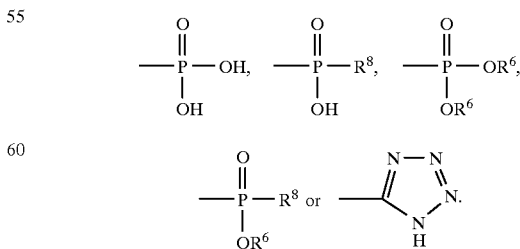

Especially preferred are compounds having the structural formula

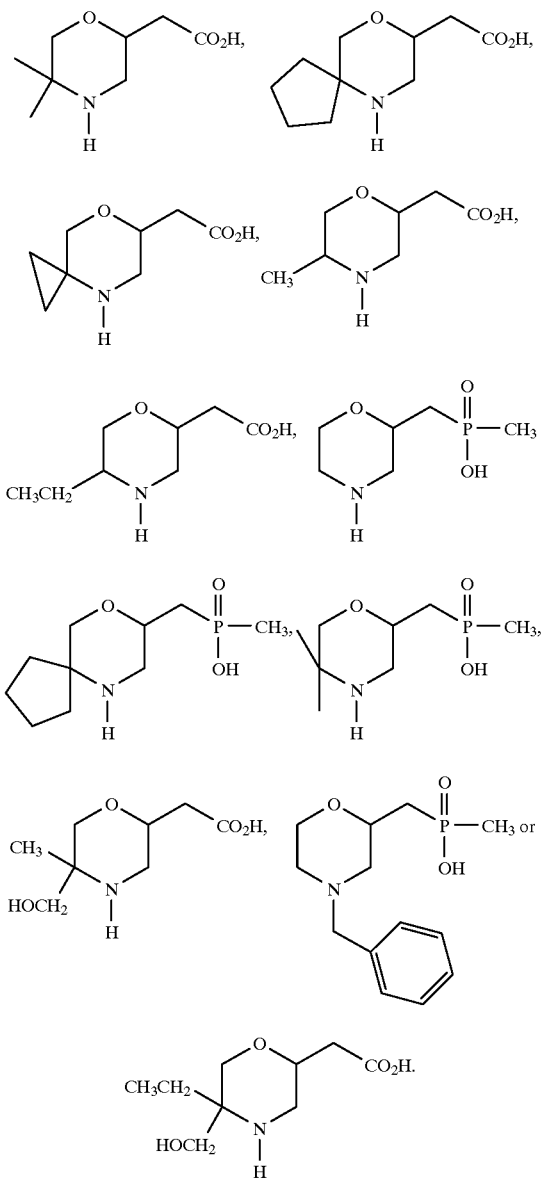

This invention also comprises a pharmaceutical composition comprising an effective amount of a compound of Formula I in combination with a pharmaceutically acceptable carrier.

This invention further comprises a method for treating petit mal seizures in a mammal comprising administering to the mammal an effective amount of a compound of Formula I.

Additionally, this invention comprises a method for treating cognitive disorders in a mammal comprising administering to the mammal an effective amount of a compound of Formula I.

This invention also comprises a method for treating respiratory depression associated with GABA$_B$ receptor stimulation comprising administering to a mammal in need of such treatment an effective amount of a compound of Formula I.

DETAILED DESCRIPTION

As used herein, the definitions of the following terms are applicable:

"alkyl" means straight or branched alkyl chains of 1 to 8 carbon atoms, and "alkoxy" similarly refers to alkoxy groups having 1 to 8 carbon atoms;

"alkanoyl" means "alkyl-C(O)—";

"alkoxycarbonyl" means "alkyl-O—C(O)—";

"cycloalkyl" means a saturated carbocyclic ring having from 3 to 8 ring members;

"halogeno" means a fluorine, chlorine, bromine or iodine radical;

"leaving group" means a group which can be readily displaced by a nucleophile, such as Cl, Br, I or an alkylsulfonyl group of the formul alkyl-SO$_3$—;

"counterion" means a cation, such as Na$^+$, K$^+$, Li$^+$, Cs$^+$, NH$_4^+$, Ca$^{++}$ or Mg$^{++}$.

Where reference is made to numbered positions of the heterocyclic ring, the numbered positions refer to numbering of the ring atoms as follows:

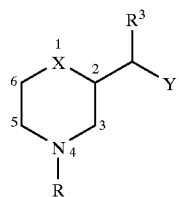

Certain compounds of the invention are acidic, e.g., those compounds which possess a carboxylic, sulfonic, phosphinic or phosphonic acid group. These compounds form pharmaceutically acceptable salts with inorganic and organic bases. Examples of such salts are the sodium, potassium and calcium salts. Also included are salts formed with pharmaceutically acceptable amines such as ammonia, alkyl amines, hydroxyalkylamines, N-methylglucamine and the like.

The salts may be formed by conventional means, as by reacting the free acid form of the product with one or more equivalents of the appropriate base in a solvent or medium in which the salt is insoluble, or in a solvent such as water which is then removed in vacuo or by freeze-drying or by exchanging the cations of an existing salt for another cation on a suitable ion exchange resin.

Certain compounds of the invention are basic, e.g. those compounds which possess a basic nitrogen atom. These compounds form pharmaceutically acceptable salts with organic and inorganic acids. Examples of suitable acids for such salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, K$_2$CO$_3$, NH$_3$ and NaHCO$_3$. The free base forms differ from their respective salt forms somewhat in certain physical properties, such as solubility in polar solvents, but the salts are otherwise equivalent to their respective free base forms for purposes of this invention.

Certain acidic or basic compounds of the present invention may exist as zwitterions.

Certain compounds of the present invention can form solvates with an appropriate pharmacologically acceptable solvent such as water. Such solvates can also form with the salts or zwitterions of compounds of the present invention, as defined above.

Compounds of the formula I have at least one asymmetrical carbon atom and therefore include various stereoisomers. The invention includes all such isomers both in pure form and in admixture, including racemic mixtures.

The following solvents and reagents employed in preparing compounds of the present invention are identified by the terms or abbreviations indicated: diethyl ether ($Et_2O$); ethyl acetate (EtOAc); methanol (MeOH); ethanol (EtOH); dimethylformamide (DMF); tetrahydrofuran (THF); acetic acid (AcOH); N,N-diisopropylethylamine (Hünig's Base); triethylamine ($NEt_3$); 1,8-diazabicyclo[5.4.0]undec-7-ene (DBU); 4-dimethylaminopyridine (DMAP); dimethylsulfoxide (DMSO); dicyclohexylcarbodiimide (DCC); 1-(3-dimethylaminopropyl)-3-ethylcarbodiimide hydrochloride (DEC); boron trifluoride etherate ($BF_3.OEt_2$); iso-propyl alcohol (IPA); triphenylphosphine (TPP); m-chloroperbenzoic acid (MCPBA).

Compounds of the present invention can be prepared via methods known to those skilled in the art. For example, compounds of the formula Ib, i.e., compounds of the formula I wherein X is O and Y is —$CO_2R^6$, can be prepared from an amino alcohol of the formula II or V with a crotonate ester of the formula III or VI, respectively, as shown in Reaction Scheme A, wherein R, $R^1$, $R^2$ and $R^3$ are as defined above, and L is a leaving group, such as Cl, Br or I. The reaction is carried out in a suitable solvent, such as $CH_2Cl_2$, in the presence of a tertiary amine base, such as $NEt_3$ or Hünig's base, to form a compound of the formula IV, from compounds II and III, or VII, from compounds V and VI. Compounds of the formula IV or VII are cyclized by heating in the presence of a suitable base, such as DBU, in a high boiling solvent, such as toluene to give a compound of the formula Ib.

Reaction Scheme A

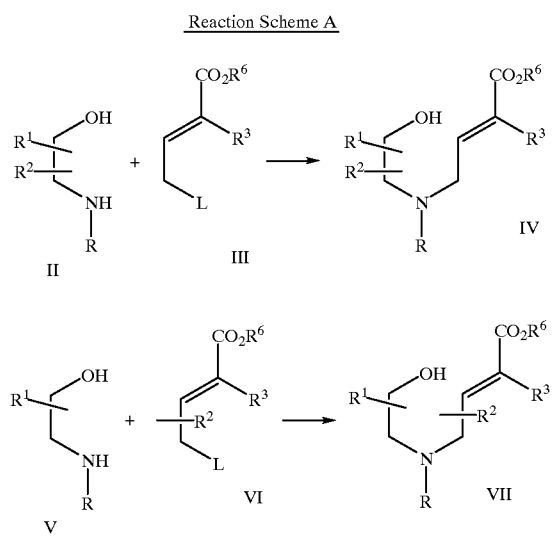

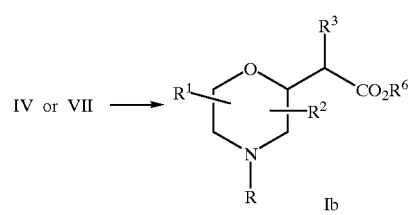

Compounds of the formula Ib, Ie or If can be converted to compounds of the formula Ic, i.e., compounds of the formula I wherein Y is —$CO_2H$, by hydrolysis with a strong inorganic acid, preferably HCl, most preferably 1N to 6N aqueous HCl.

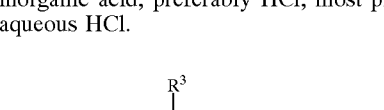

Compounds of the formula Ib, wherein R is H, or compounds of the formula Ie, can be converted to compounds of the formula If, i.e., compounds of the formula I, wherein Y is —$CO_2R^6$ and R is $C_1$-$C_8$ alkyl, $C_1$-$C_8$ alkanoyl, $C_1$-$C_8$ alkoxycarbonyl, $C_3$-$C_8$ cycloalkyl, $C_3$-$C_8$ cycloalkyl($C_1$-$C_8$)alkyl, Ar—($C_1$-$C_8$)alkyl and Ar—$CH_2$—O—C(O)—, and Ar is as defined above, by alkylation or acylation with a compound of the formula R—L, wherein R is $C_1$-$C_8$ alkyl, $C_1$-$C_8$ alkanoyl, $C_1$-$C_8$ alkoxycarbonyl, $C_3$-$C_8$ cycloalkyl, $C_3$-$C_8$ cycloalkyl($C_1$-$C_8$)alkyl, Ar—($C_1$-$C_8$) alkyl and Ar—$CH_2$—O—C(O)—, Ar is as defined above, and L is a leaving group, such as Cl, Br or I.

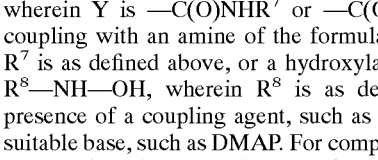

Compounds of the formula Ic can be converted to compounds of the formula Id, i.e., compounds of the formula I wherein Y is —C(O)$NHR^7$ or —C(O)—N(OH)—$R^8$, by coupling with an amine of the formula $R^7$—$NH_2$, wherein $R^7$ is as defined above, or a hydroxylamine of the formula $R^8$—NH—OH, wherein $R^8$ is as defined above, in the presence of a coupling agent, such as DCC or DEC, and a suitable base, such as DMAP. For compounds of the formula Ic wherein R is H, the nitrogen of the morpholine ring can be protected with a suitable amine protecting group prior to the coupling reaction, followed by deprotection when the reaction is complete. Similarly, the hydroxy portion of the hydroxylamine can be protected using a suitable hydroxyl protecting group prior to the coupling reaction, followed by deprotection when the reaction is complete.

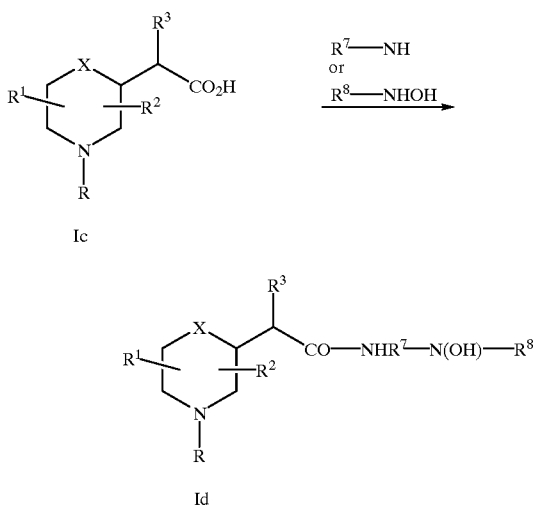

Ic

Id

Compounds of the formula Ie, i.e., compounds of the formula I wherein X is S, and Y is —$CO_2R^6$, wherein $R^6$ is as defined above, are prepared by reacting a thiazolidine of the formula VIII or X and a crotonate derivative of the formula VI or III, respectively, as shown in Reaction Scheme B, wherein R, $R^1$, $R^2$ and $R^3$ are as defined above. The reaction is carried out in a suitable solvent, such as THF, in the presence of a tertiary amine base, such as $NEt_3$ or Hünig's base, to give a compound of the formula IX, from compounds of the formula VIII and VI, or a compound of the formula XI, from compounds of the formula X and III. Compounds of the formula IX or XI are cyclized by heating in an alcohol solvent, such as methanol, in the presence of a strong inorganic acid, such as HCl, preferably 6N aqueous HCl, to give compounds of the formula Ie.

Reaction Scheme B

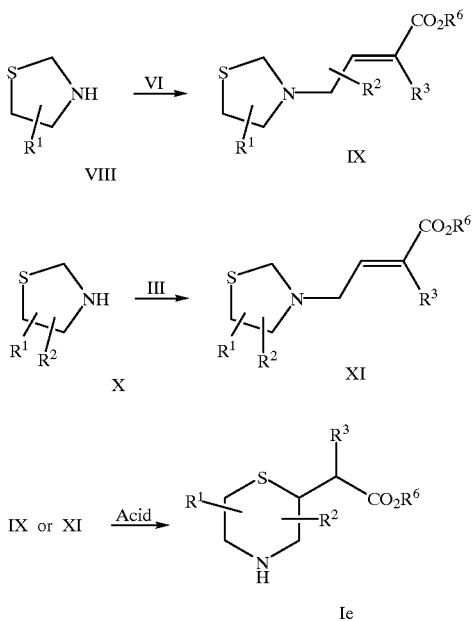

In an alternative method for preparing compounds of the formula Ie, an aziridine of the formula XII or XIV is reacted with a compound of the formula VI or III, respectively, as shown in Reaction Scheme C, wherein R, $R^1$, $R^2$ and $R^3$ are as defined above. The reaction is carried out in a suitable solvent, such as THF, in the presence of a tertiary amine base, such as $NEt_3$ or Hünig's base, to give a compound of the formula XIII, from compounds of the formula XII and VI, or a compound of the formula XV, from compounds of the formula XIV and III. Compounds of the formula XIII or XV are treated with thioacetic acid to form compounds of the formula XVI or XVII, respectively, which are hydrolyzed with a strong base, such as NaOH, preferably 1N NaOH (aqueous), and acidified using a strong inorganic acid, such as HCl, preferably about 6N aqueous HCl, to give a compound of the formula Ie.

Reaction Scheme C

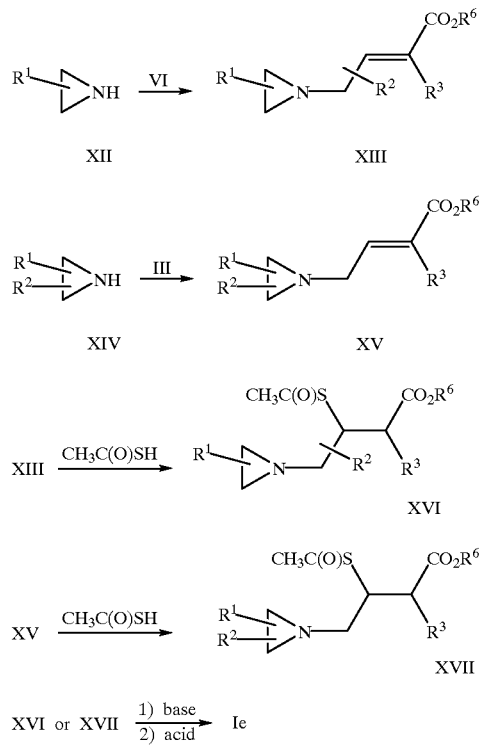

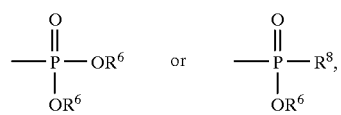

Compounds of the formula Ig, i.e., compounds of the formula I, wherein X is O and Y is

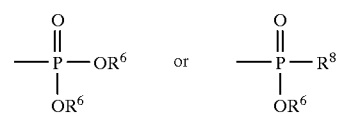

are prepared by reacting a compound of the formula II or V with a compound of the formula XVIII or XIX, respectively, as shown in Reaction Scheme D, wherein Q represents $$-\overset{O}{\underset{OR^6}{\overset{\|}{P}}}-OR^6 \quad \text{or} \quad -\overset{O}{\underset{OR^6}{\overset{\|}{P}}}-R^8$$

and R, $R^1$, $R^2$, $R^3$, $R^6$ and $R^8$ are as defined above. The reaction is carried out by heating a mixture of II and XVIII, or V and XIX, in a suitable solvent, such as toluene, in the presence of a strong organic base, such as DBU. For compounds of the formula Ig wherein R is H, the nitrogen of the morpholine ring can be protected with a suitable amine protecting group prior to the coupling reaction, followed by deprotection when the reaction is complete.

Reaction Scheme D

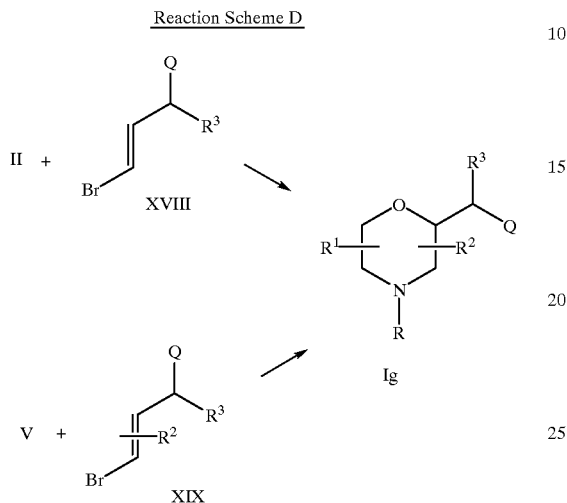

Compounds of the formula XVIII and XIX are prepared from dibromides of the formula XX and XXI, respectively, wherein $R^2$ and $R^3$ are as defined above, by reacting with a compound of the formula $P(R^8)(OR^6)_2$ or $P(OR^6)_3$, wherein $R^6$ and $R^8$ are as defined above.

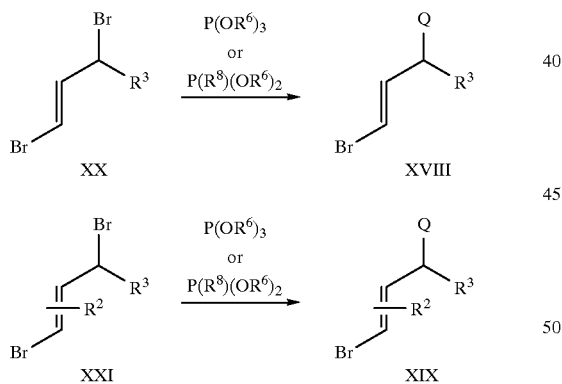

Compounds of the formula Ig or Im can be converted to compounds of the formula Ih wherein Z is —OH or —$R^8$ and $R^8$ is as defined above, i.e., compounds of the formula I wherein X is O or S, and Y is

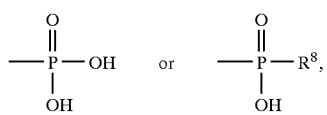

by hydrolysis using a base, such a NaOH.

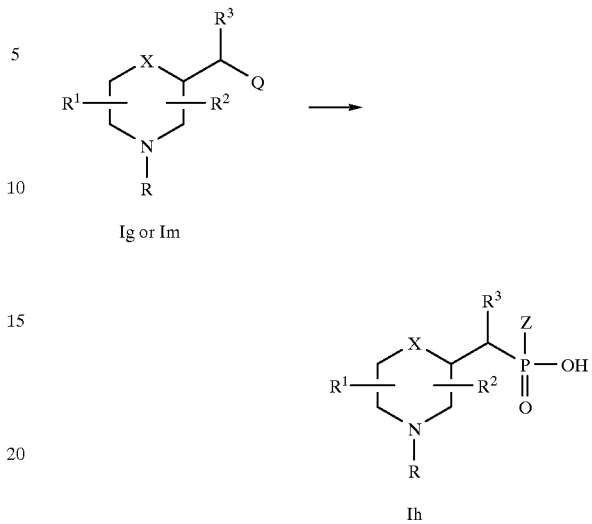

Compounds of the formula Ig are also prepared by reacting a compound of the formula XXII, wherein L is a leaving group, preferably 1, and R, $R^1$, $R^2$ and $R^3$ are as defined above, with a compound of the formula $P(R^8)(OR^6)_2$ or $P(OR^6)_3$, wherein $R^6$ and $R^8$ are as defined above.

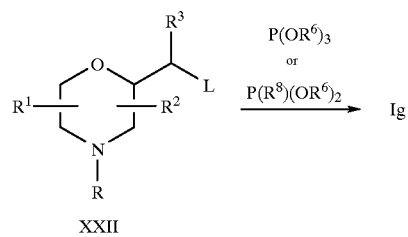

Compounds of the formula Ih, i.e., compounds of the formula I, wherein X is O, Y is —$SO_3H$, L is a leaving group and R, $R^1$, $R^2$ and $R^3$ are as defined above, are prepared from compounds of the formula XXII by the method shown in Reaction Scheme E. A compound of the formula XXII is reacted with a commercially available thiol of the formula Pr-SH, wherein Pr is a suitable sulfur protecting group, such as benzyl, to form a sulfide of the formula XXIII. The sulfide XXIII is deprotected and the resulting thiol XXIV is oxidized to give a compound of the formula Ih.

Reaction Scheme E

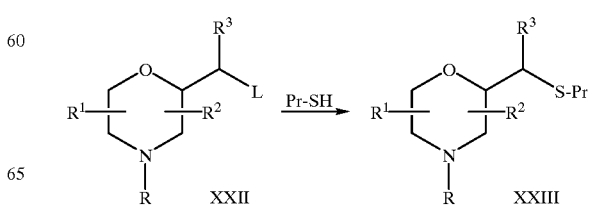

XXIII $\xrightarrow{\text{deprotect}}$ 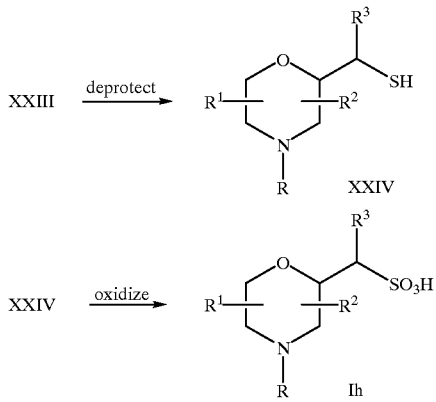

XXIV $\xrightarrow{\text{oxidize}}$

Compounds of the formula Ii, i.e., compounds of the formula I, wherein X is O and Y is

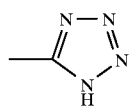

are prepared from compounds of the formula XXII as shown in Reaction Scheme F, wherein R, $R^1$, $R^2$ and $R^3$ are as defined above. A compound of the formula XXII is reacted with a cyanide salt, such as NaCN or KCN, to form a compound of the formula XXV. Compounds of the formula XXV are treated with sodium azide and ammonium chloride to form compounds of the formula Ii.

Reaction Scheme F

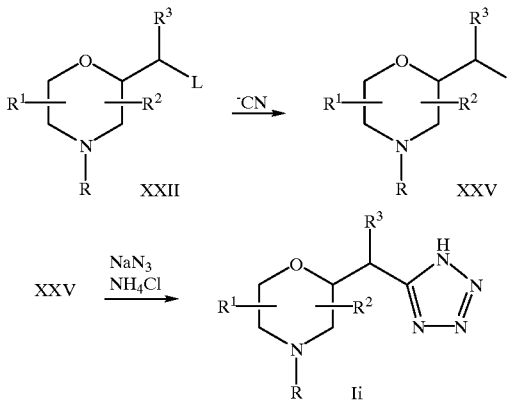

Compounds of the formula I wherein X is O and Y is —$SO_3R^6$ or —$SO_2NHR^7$ are prepared from compounds of the formula Ih via known methods.

Compounds of the formula Ik, i.e., compounds of the formula I, wherein X is S and Y is

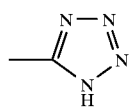

are prepared from compounds of the formula Ie or If (wherein X is S) as shown in Reaction Scheme G, wherein R, $R^1$, $R^2$, $R^3$ and $R^6$ are as defined above. A compound of the formula Ie or If is reacted with ammonia to form a primary amide of the formula XXVI. The amide XXVI is dehydrated to form a nitrile of the formula XXVII, which is converted to a compound of the formula Ik by treating with sodium azide and ammonium chloride. Where a compound of the formula Ie is used in Reaction Scheme G, the nitrogen of the thiomorpholine ring can be protected with a suitable amine protecting group, such as benzyl or benzyloxycarbonyl, prior to treatment with ammonia. Compounds of the formula Ik where R is H are then obtained by deprotection after tetrazole formation.

Reaction Scheme G

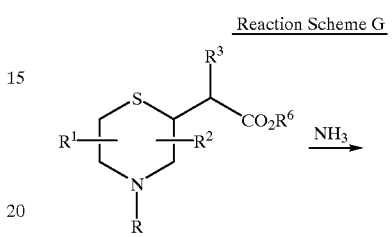

Ie or If (wherein X is S)

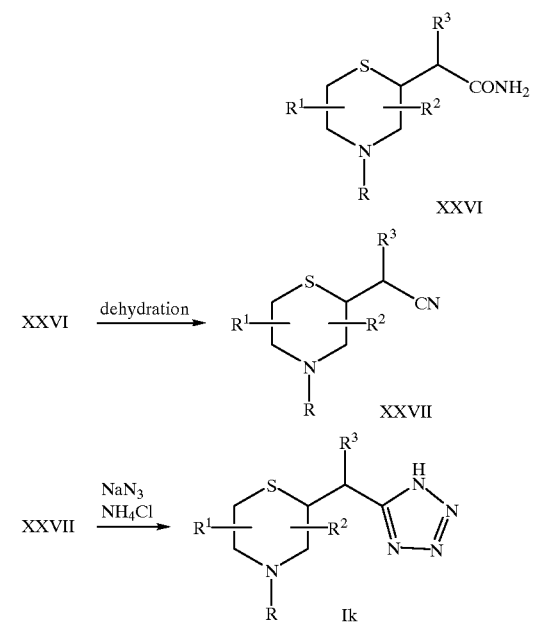

Compounds of the formula Im, i.e., compounds of the formula I wherein X is S and Y is

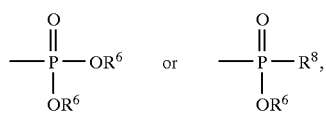

are prepared by reacting an aziridine of the formula XII or XIV with a compound of the formula XXVIII or XXX, respectively, as shown in Reaction Scheme H, wherein R, $R^1$, $R^2$, $R^3$, $R^6$ and $R^8$ are as defined above. The reaction is carried out in the presence of a tertiary amine base, such as $NEt_3$ or Hünig's base, to give a compound of the formula XXIX, from compounds of the formula XII and XXVIII, or a compound of the formula XXXI, from compounds of the formula XIV and XXX. Compounds of the formula XXIX or XXXI are treated with thiolacetic acid, optionally in the presence of a Lewis acid, such as $BF_3 \cdot OEt_2$, to form a thiolacetate of the formula XXXII or XXXIII, respectively. Cyclization by treating XXXII or XXXIII in a suitable solvent with dilute base, such as 1N to 2N NaOH (aqueous), gives rise to a compound of the formula XXXIV. Compound XXXIV is reacted with a compound of the formula R—L, as defined, to form a compound of the formula XXXV. The hydroxyl group of XXXV is converted to a leaving group LG, selected from —Br, —I and —OSO$_2$CF$_3$, by treating with HBr, HI or trifluoromethanesulfonic anhydride, and the resulting compound XXXVI treated with a compound of the formula P(R$^8$)(OR$^6$)$_2$ or P(OR$^6$)$_3$, wherein R$^6$ and R$^8$ are as defined above, to form a compound of the formula Im, wherein Q is as defined above. For compounds of the formula Im wherein R is H, the nitrogen of the thiomorpholine ring of compound XXXIV can be protected with a suitable amine protecting group, in which case the reaction with R—L is not performed. Deprotection after completion of the reaction scheme results in the formation of a compound of the formula Im wherein R is H.

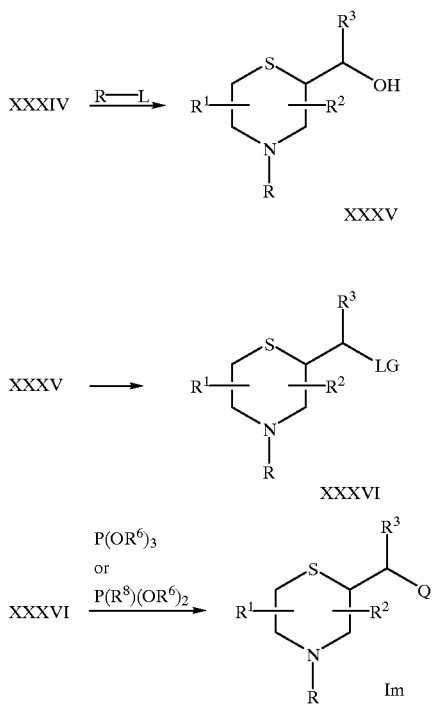

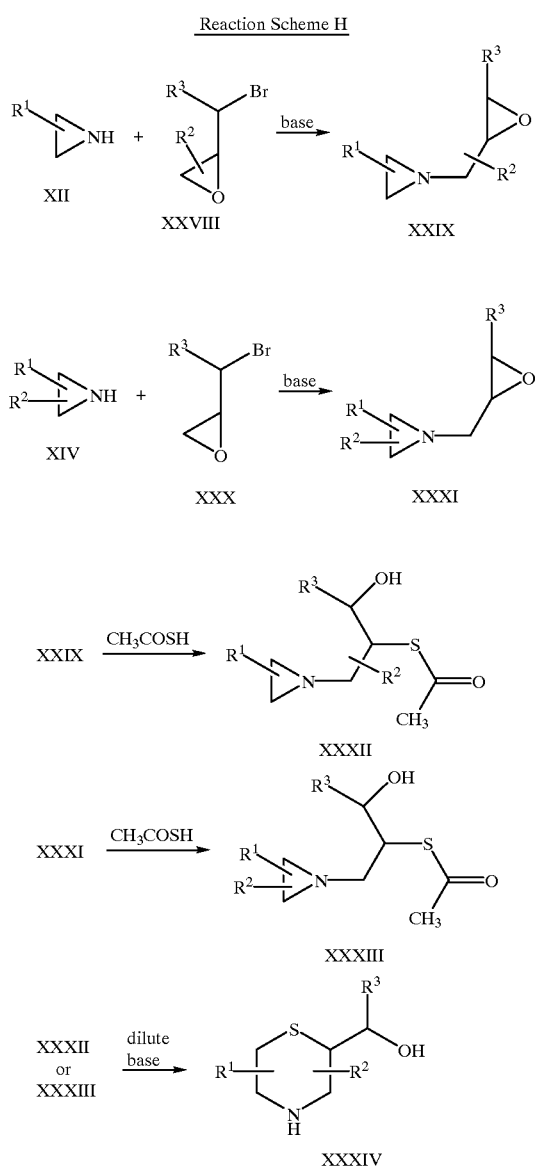

Compounds of the formula In, i.e., compounds of the formula I wherein X is O and Y is —SO$_2$H or —SO$_3$H, are prepared by reacting a chloride of the formula XLI, wherein R, R$^1$, R$^2$ and R$^3$ are as defined above, with 2-mercaptobenzotriazole (XLII), wherein

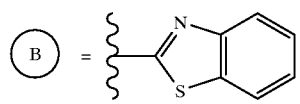

as shown in Reaction Scheme J. The reaction is carried out by heating in a suitable solvent, such as DMF, in the presence of a base, such as K$_2$CO$_3$ or Cs$_2$CO$_3$ to give the product XLIII. The product XLIII is oxidized with a suitable oxidizing agent, such as MCPBA, to form the sulfonyl derivative XLIV. The sulfonyl derivative XLIV is then reduced by treating with a suitable reducing agent, such as NaBH$_4$, to form a sulfinate of the formula XLV, wherein M$^+$ is a suitable counterion, such as Na$^+$ or NH$_4^+$. The sulfinate XLV can be further oxidized to the analogous sulfonate XLVI by treating with a suitable oxidizing agent, such as MCPBA. The sulfinate XLV or the sulfonate XLVI is then treated with TPP to form a compound of the formula In. Compounds of the formula In where R is H can be prepared by hydrogenation of a compound of the formula In wherein R is benzyl, in the presence of a suitable catalyst, such as 5% or 10% Pd/C. Compounds of the formula In are generally isolated as the zwitterion, as shown in Reaction Scheme J.

Reaction Scheme J

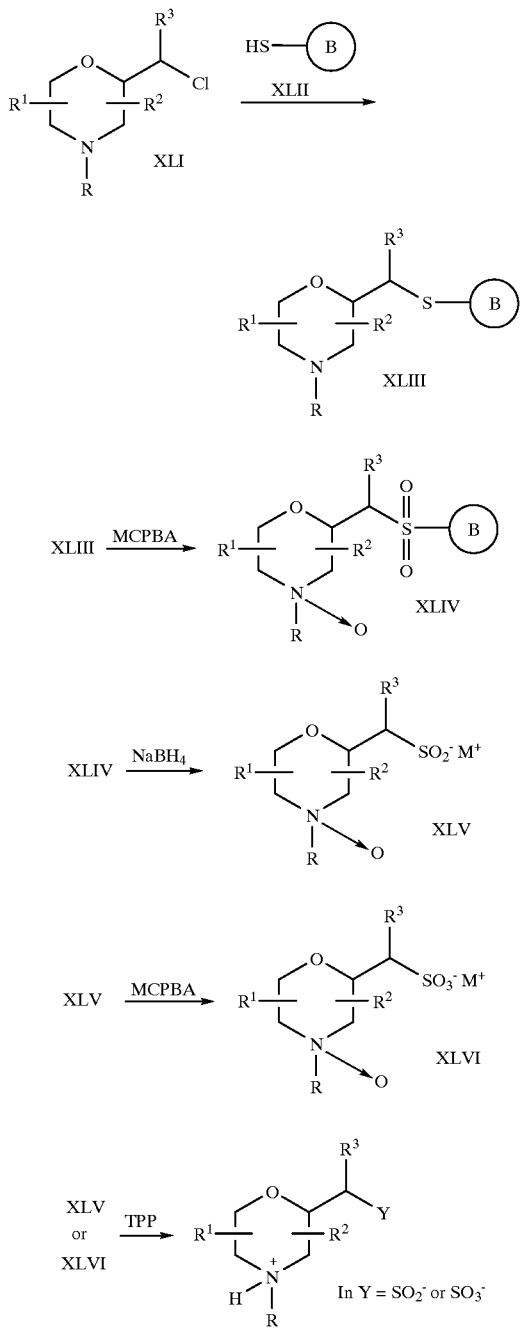

Reaction Scheme K

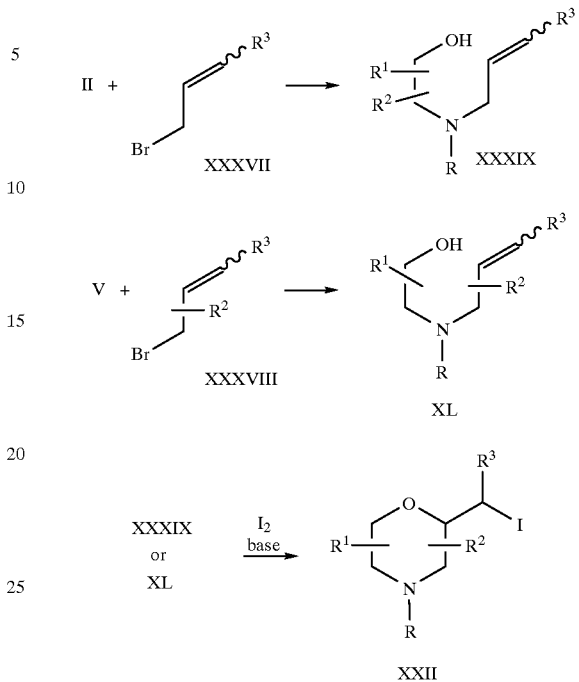

Starting compounds of the formula XXII are known, as disclosed in EP 311948 and EP 398426, or can be prepared by reacting a compound of the formula II or V with an allyl bromide XXXVII or XXXVIII, respectively, as shown in Reaction Scheme K, to form a compound of the formula XXXIX, from compounds of the formula II and XXXVII, or XL, from compounds of the formula V and XXXVII. Compounds of the formula XXXIX and XL are converted to compounds of the formula XXII by treating with iodine in the presence of a suitable base.

Starting compounds of the formulae II, III, V, VI, VIII, XII, XIV, XX, XXI, XXVII, XXX, XXXVII, XXXVII, XLI and XLII are either commercially available or can be prepared from commercially available starting materials using known methods.

Reactive groups not involved in the above processes can be protected during the reactions with conventional protecting groups which can be removed by standard procedures after the reaction. The following table shows some typical protecting groups:

| Group to be protected | Protected Group |
|---|---|
| —COOH | —COOalkyl, —COObenzyl, —COOphenyl |
| ⟩NH | ⟩NCOalkyl, ⟩NCObenzyl, ⟩NC(O)C$_6$H$_5$, ⟩NCH$_2$OCH$_2$CH$_2$Si(CH$_3$)$_3$, ⟩NC(═O)OC(CH$_3$)$_3$ |
| ⟩C═O | (cyclic acetals), ⟩C(Oalkyl)$_2$ |
| —OH | —OCH$_3$ |

-continued

| Group to be protected | Protected Group |
|---|---|
| —NH$_2$ | 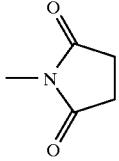 |

The compounds of the invention possess GABA$_B$ antagonistic properties. The compounds of the invention are, therefore, useful when stimulation of GABA$_B$ receptors is a factor in the disease or disorder. This includes treatment or prevention of: central nervous system disorders, including anxiety, depression, general absence or petit mal seizures and conditions requiring enhancement of cognitive performance; and respiratory depression associated with GABA$_B$ receptor stimulation, e.g. such as occurs during baclofen treatment.

The utility of the compounds of the present invention as GABA$_B$ antagonists is demonstrated by using the following in vitro assay procedures:

GABA$_B$ Receptor Binding Assay

The percentage inhibition of GABA binding to GABA$_B$ receptors is measured by tritiated GABA ([$^3$H]GABA) determination of the degree of binding by scintillation counting. Rat brain synaptosomes are used as a source of GABA$_B$ receptors. An incubation medium is prepared from the following: 20 μg/mL of the compound to be tested as a solution in 1% DMSO/water; 5 nM [$^3$H]GABA; 50 mM Tris buffer (pH 7.5); and 2.5 mM CaCl$_2$. The medium also contains 40 μM isoguvacine to selectively block binding to GABA$_A$ receptors. The synaptosome (200 μg/mL) is added to the incubation medium and incubated for 30 minutes at 20° C. The incubation is terminated by filtration and counted to determine the percentage inhibition of [$^3$H]-GABA binding. The results are reported as IC$_{50}$ values for those compounds inhibiting [$^3$H]-GABA binding by >50%.

In Vitro Assay

Male Hartley guinea pigs (450–650 g) are sacrificed by stunning and the trachea removed proximal to the carina and cut into 5 mm segments. The segments are attached to isometric force displacement transducers (Model FT03: Grass Instruments) and suspended in 15 mL organ baths filled with low Ca$^{2+}$ (0.6 mmol/L) Tyrode's buffer solution (pH 7.4) supplemented with 5.6 mmol/L glucose, 30 μmol/L choline and 2 μmol/L indomethacin. The solution is bubbled with a mixture of 95% O$_2$+5% CO$_2$ and maintained at 37° C. The tracheal segments are allowed to equilibrate for 90 minutes under a resting tension of 0.5 g.

Platinum electrodes are placed on either side of the trachea and electrical field stimulation (EFS) (20 V, 8 Hz, 0.5 ms pulse for 5 s) was generated each minute from an electrical stimulator (Model S-88: Grass Instruments) and delivered to the electrodes through a stimulus distributor (Buxco Electronics). The stimulation parameters are chosen as appropriate for producing cholinergic contractions of the trachea that are sensitive to the inhibitory effects of compounds acting at prejunctional GABA$_B$ receptors. Contractile responses were recorded on a polygraph (Harvard Apparatus). The compound to be tested is added to the bath 10 min. before addition of 30 μmol/L baclofen. The effect of baclofen treatment in the absence or in the presence of the compound to be tested is expressed as a percent inhibition of EFS-induced contractions. For compounds that caused greater than 30% inhibition of the response to 30 μmol/L baclofen, results are expressed as IC$_{30}$ values.

The utility of the compounds of the present invention is further demonstrated by using the following in vivo test procedures.

Animal Models for Absence Seizures

A. Snead, Eur. J. Pharmacol., 213, 343–349 (1992), teaches a pharmacological model for testing the effectiveness of GABA$_B$ antagonists in preventing seizures induced by intra-peritoneal (ip) administration of either γ-butyrolactone (GBL) or pentylenetetrazole (PTZ) to rats. The animal is treated with the test compound, then monitored after being subjected to a dose of either GBL or PTZ sufficient to induce seizures. The in vivo activity of the compounds of the present invention can be demonstrated using the procedures described therein.

B. Hosford, et al., Science, 257, 398–401 (Jul. 17, 1992), teaches a pharmacological model for testing the effectiveness of GABA$_B$ antagonists as anticonvulsants for the treatment of absence seizures by administering the compound to be tested to lethargic (lh/lh) mice, a mutant strain with spontaneous seizures. The in vivo activity of the compounds of the present invention can be demonstrated using the procedures described therein.

Animal Model for Respiratory Depression:

Place unanesthetized guinea pigs in a head-out plethysmograph and expose to a CO$_2$ enriched gas mixture (10% CO$_2$, 21% O$_2$, 69% N$_2$) for 10 min., (see Danko, et al., J. Pharm. Methods, 19, 165–173 (1988)). Plethysmograph pressure is detected with a transducer connected to a chart recorder. Minute ventilation is calculated as the product of tidal volume and respiratory frequency. The compound to be tested is administered orally, subcutaneously (sc), intraperitoneally (ip) or via an intracerebroventricular route (icv). Baclofen (3 mg/kg, sc) was given 30 min before exposure to the CO$_2$ enriched gas. When given by the oral route, the compounds is administered 1, 3, 5 or 7 h before exposure to CO$_2$ enriched gas. A 40 or 30 min. preteratment is used for the subcutaneous and intraperitoneal routes, respectively. The vehicle for oral, sc or ip administration is saline. For icv administration, single icv cannulae are placed in the lateral ventricle of anesthetized guinea pigs, (see McLeod, et al., Eur. J. Pharmacol., 209, 141–142 (1988)). The animals are allowed to recover approximately one week prior to use for ventilation experiments. The vehicle for icv administration is artificial cerebrospinal fluid (CSF).

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 10 mg to 3000 mg, more preferably from about 30 mg to 1000 mg, according to the particular application. The appropriate dosage can be determined by comparing the activity of the compound with the activity of a known $GABA_B$ antagonist such as CGP 35348.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts or solvates thereof will be regulated according to the judgment of the attending clinician considering such factors as age, condition and size of the patient as well as severity of the symptoms being treated. A typical recommended dosage regimen is oral administration of from 10 mg to 3000 mg/day preferably 30 to 1000 mg/day, in one to four divided doses to achieve relief of the symptoms. The compounds are non-toxic when administered within this dosage range.

Following are illustrative examples of procedures for preparing compounds of formula I.

PREPARATIVE EXAMPLE 1

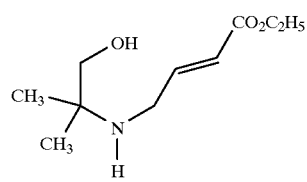

Add 5.2 mL of Hünig's Base to a solution of 1.8 g of 2-amino-2-methyl-1-propanol and 3.3 mL of ethyl 4-bromocrotonate in 40 mL of $CH_2Cl_2$. Stir the solution at room temperature for 24 h, then concentrate under reduced pressure to a residue. Suspend the residue in 60 mL of EtOAc and stir for 0.5 h, then filter. Concentrate the filtrate under reduced pressure to yield a crude product. Purify the product by flash chromatography (silica gel, 95:5 $CH_2Cl_2$:MeOH/$NH_3$) to yield 2.5 g of the title compound, mp 71–73° C.

PREPARATIVE EXAMPLE 2

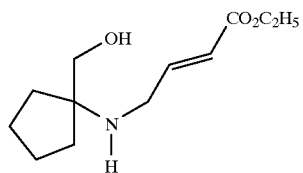

Add 5 g of ethyl 4-bromocrotonate and 6 mL of $NEt_3$ to a solution of 2 g of 1-aminocyclopentanemethanol in 60 mL of EtOH. Heat the solution at reflux temperature for 18 h, then cool to room temperature and concentrate in vacuo to a residue. Dissolve the residue in 150 mL of water and extract with 4×50 mL of $CH_2Cl_2$. Wash the combined organic extracts with water and then with brine. Dry the organic extracts using $MgSO_4$, filter and evaporate the filtrate under reduced pressure to produce 1.85 g of crude product. Purify by flash chromatography (silica gel, $CH_2Cl_2$/ 10% MeOH) to yield 0.67 g of the title compound.

PREPARATIVE EXAMPLE 3

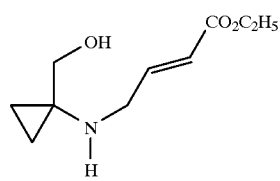

Suspend 4 g of 1-aminocyclopropanemethanol hydrochloride in 60 mL of EtOH. Add 10 mL of $NEt_3$ and stir the mixture at room temperature for 0.5 h. Add 8 g of ethyl 4-bromocrotonate and stir for 18 h. Concentrate in vacuo to a residue. Dissolve the residue in 150 mL of water and extract with 4×50 mL of $CH_2Cl_2$. Wash the combined organic extracts with brine, dry over $MgSO_4$, then filter and concentrate in vacuo to yield 4.5 g of crude product. Purify by flash chromatography (silica gel, EtOAc) to yield 2.1 g of the title compound. $^1$H-NMR shows the cyclopropyl protons at ca. δ=0.55 and 0.75 ppm, and the vinyl protons at ca. δ=6.04 and 7.05 ppm.

PREPARATIVE EXAMPLE 4

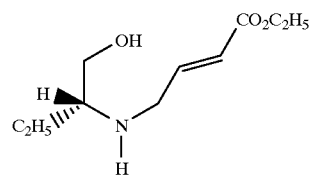

Add 10 mL of $NEt_3$ to a mixture of 5 g of (R)—(—)-2-amino-1-butanol and 13 g of ethyl 4-bromocrotonate in 120 mL of $CH_2Cl_2$. Stir the solution at room temperature for 4 h. Add $CH_2Cl_2$ sufficient to bring the total volume to 250 mL and wash with 3×100 mL of brine. Concentrate the $CH_2Cl_2$ solution in vacuo to yield 6.2 g of crude product. Purify by flash chromatography (silica gel, 30:1 EtOAc:MeOH) to yield 2.2 g of the title compound. $^1$H-NMR ($CDCl_3$) δ values in ppm: 7.06 (d of t, 1H); 6.07 (d of t, 1H); 4.26 (q, 2H); 3.34–3.75 (m, 4H); 1.55 (m, 2H); 1.34 (t, 3H); 0.97 (t, 3H).

PREPARATIVE EXAMPLE 5

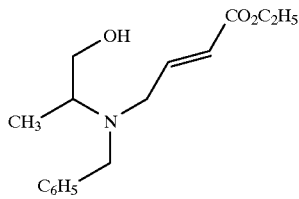

Combine 3.3 g of 2-benzylamino-1-propanol, 4 mL of ethyl 4-bromocrotonate, and 25 mMol of DBU in 100 mL of toluene and heat the mixture at reflux for 24 h. Concentrate in vacuo to a residue and dissolve the residue in $CH_2Cl_2$/$H_2O$ (100 mL/400 mL). Separate the aqueous layer and extract with 3×100 mL of $CH_2Cl_2$. Combine the organic layers and wash with brine. Dry the combine organic layers over $MgSO_4$, filter, then concentrate in vacuo to yield 4.2 g of crude product. Purify by flash chromatography (silica gel, 1:1 hexane/EtOAc) to produce 2.4 g of the title compound.

PREPARATIVE EXAMPLE 6

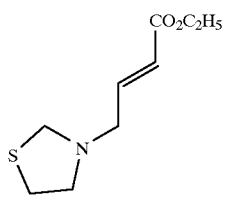

Prepare a solution of 1.6 mL of thiazolidine and 3 mL of $NEt_3$ in 30 mL of THF. Stir the solution, add 4.5 mL of ethyl 4-bromocrotonate, and stir the resulting mixture at room temperature for 60 h. Dilute the reaction mixture with 300 mL of EtOAc, wash with water and then with brine, and dry over $MgSO_4$. Concentrate the organic solution in vacuo to yield 5.4 g of crude product. Purify by flash chromatography (silica gel, 2:1 hexane/EtOAc) to produce 4 g of the title compound. This was used in the next step without further purification. (Example 18)

PREPARATIVE EXAMPLE 7

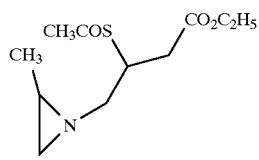

Step A:

Add 10 mL of $NEt_3$ to a solution of 9.2 mL of ethyl 4-bromocrotonate and 4 mL of 2-methylaziridine in 100 mL of THF. Stir for 60 h, during which time a white precipitate forms. Dilute the reaction mixture with 300 mL of EtOAc and wash with water and then with brine. Dry the organic solution over $MgSO_4$, filter, and concentrate in vacuo to yield 6.7 g of crude product. Purify by flash chromatography (silica gel, 1:4 hexane/EtOAc) to yield 5.2 g of E-4-(2-methyl-1-aziridinyl)-2-butenoic acid ethyl ester.

Step B:

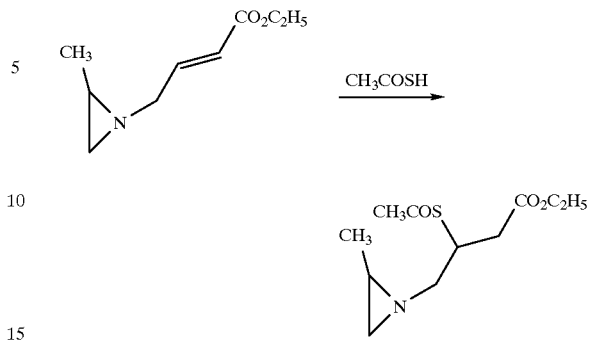

Treat 1.03 g of the product of step A with 0.5 mL of $CH_3COSH$ (as described in *J. Am. Chem. Soc.*, 77, 5144 (1955)) at 0° C. and stir the mixture for 18 h. Confirm completion of the reaction by $^1$H-NMR. Purify the mixture directly by flash chromatography (silica gel, EtOAc), to yield 1 g of the title compound.

PREPARATIVE EXAMPLE 8

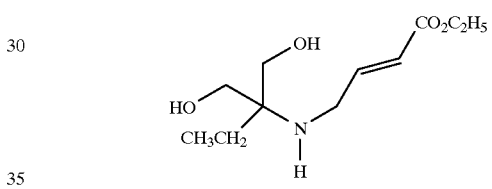

Dissolve 5 g of 2-amino-2-ethyl-1,3-propanediol and 9 g of ethyl 4-bromocrotonate in 60 mL of THF. Add 15 mL of $NEt_3$ and stir at room temperature for 70 h. Dilute the reaction mixture with 300 mL of water, extract with 3×150 mL of $CH_2Cl_2$, wash with brine, and dry over $MgSO_4$. Concentrate the combined extracts in vacuo to yield 5.5 g of crude product. Purify by flash chromatography (silica gel, 95:5 EtOAc/MeOH) to yield 2.2 g of the title compound.

Using substantially the same procedure 2-amino-2-methyl-1,3-propanediol is converted to the following compound (Preparative Example 8A):

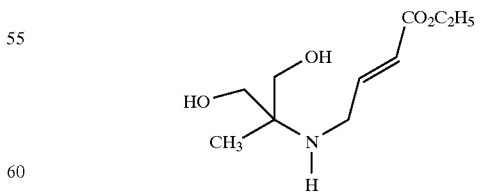

mass spectrum (FAB) m/e 218 (M+1)$^+$=100% Elemental Analysis: calcd. for $C_{10}H_{19}NO_4$; C, 55.28; H, 8.81; N, 6.45. Found; C, 54.83; H, 8.58; N, 6.40

PREPARATIVE EXAMPLE 9

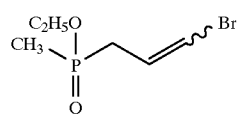

Cool 1.3 mL of diethyl methylphosphonite to 0° C., then slowly add (dropwise) 1 mL of a mixture of E- and Z-1,3-dibromo-propene. Stir the mixture at 0° C. for 30 min., then allow the mixture to warm to room temperature and stir for 3 h. Add 0.7 mL of diethyl methylphosphonite and stir for 18 h. at room temperature. Concentrate under vacuum to give the title compound as a residue.

PREPARATIVE EXAMPLE 10

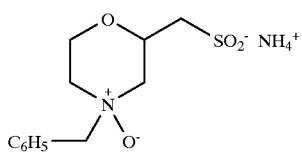

Mass Spec. (FAB): $(M+1)^+$ m/z=357

Step a:

Combine 1.13 g (5 mmol) of 4-benzyl-2-chloromethylmorpholine and 10 mL of DMF, add 0.84 g of 2-mercaptobenzothiazole and 3 g of $Cs_2CO_3$ and stir at room temperature for a short time. Heat the mixture to 100°–105° C. and monitor the reaction by TLC (silica gel, 80:20 hexane/EtOAc). Cool the mixture to room temperature when the reaction is complete and add 100 mL of $Et_2O$, filter and wash the solid residue with $Et_2O$. Wash the filtrate twice with $H_2O$ and concentrate to a residue. Purify the residue by column chromatography (silica gel, 85:15 hexane/EtOAc), to give the product

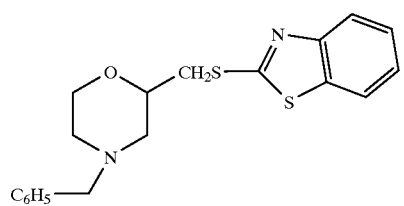

Step b:

Combine 1 g of the product of step a and 40 mL of $CH_2Cl_2$, stir while cooling to −20° to −15° C., and add 1.27 g of MCPBA. Monitor the reaction by TLC (silica gel, 91.5:7.5:1 $CH_2Cl_2$/MeOH/$NH_3$ (aqueous)). Add another 0.13 g of MCPBA and stir at 0° C. until the reaction is complete by TLC.

Wash the reaction mixture successively with 50 mL of 2% $NaHSO_3$ (aqueous), 100 mL of saturated $NaHCO_3$ (aqueous), and brine, then dry over $Na_2SO_4$. Concentrate resulting organic solution in vacuo to a residue and purify by column chromatography (silica gel, 2%–10% MeOH in $CH_2Cl_2$+a few drops of $NH_3$ (aqueous)), to give the oxidized product of formula

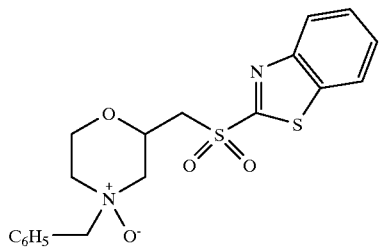

Mass Spec. (FAB): $(M+1)^+$ m/z=405

Step c:

Combine 1 g of the product of step b and 30 mL of EtOH. Stir the mixture at room temperature and add 0.195 g of $NaBH_4$. Stir for 2 days, then concentrate in vacuo to a residue and purify by column chromatography (silica gel, 67% $CH_2Cl_2$:30% MeOH:3%$NH_3$(aqueous), then 56% $CH_2Cl_2$:40% MeOH:4%NH3(aqueous)) to give the product. Dissolve the product in deionized $H_2O$ and pass through a strongly acidic ion exchange column in the $NH_4^+$ form. Concentrate the resulting solution in vacuo to give the title compound, m.p. =95°–99° C. Mass Spec. (FAB): $(M+1)^+$ m/z=272.

EXAMPLE 1

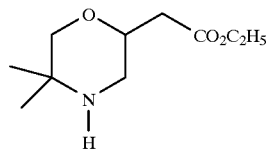

Dissolve 1.78 g of the product of Preparative Example 1 and 0.18 g of DBU in 50 mL of toluene and heat the solution at reflux for 18 h. Cool the reaction mixture and remove the solvent under reduced pressure. Purify the resulting residue by flash chromatography (silica gel, 95:5 $CH_2Cl_2$: MeOH/$NH_3$) to yield 1.2 g of the title compound.

Using substantially the same procedure the following compounds can also be prepared:

from the product of Preparative Example 3

EXAMPLE 1A

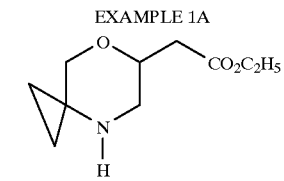

from the product of Preparative Example 2

EXAMPLE 1B

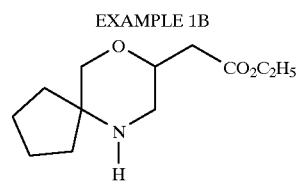

EXAMPLE 2

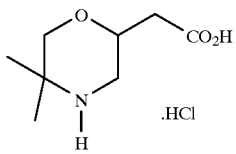

Dissolve 0.6 g of the product of Example 1 in 10 mL of 6N HCl (aqueous). Heat the solution at reflux for 18 h, then concentrate in vacuo to yield 0.5 g of the title compound, m.p. 204–206° C. Elemental Analysis, calcd. for $C_8H_{15}NO_3 \cdot HCl$; C, 45.82; H, 7.69; N, 6.68. Found, C, 45.73; H, 7.62; N, 6.41.

EXAMPLE 3

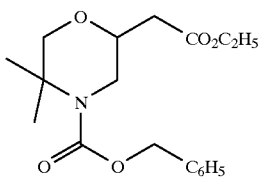

Dissolve 6.6 g of the product of Example 1, 0.2 g of DMAP, and 10 mL of benzyl chloroformate in 200 mL of $CH_2Cl_2$. Stir the solution and slowly add 10 mL of $NEt_3$ over a period of about 10 min. Stir the reaction mixture at room temperature for 6 h, then dilute with 300 mL of $CH_2Cl_2$. Wash with 2×100 mL of water, and 150 mL of brine. Dry the organic layer ($MgSO_4$), then concentrate in vacuo to yield 14.5 g of crude product. Purify by flash chromatography (silica gel, 80:20 hexane:EtOAc) to yield 9.1 9 of the title compound, m.p. =45.5°–46.5° C. Elemental Analysis: calcd. for $C_{18}H_{25}NO_5$: C, 64.45; H, 7.51; N, 4.17; found: C, 64.51; H, 7.44; N, 4.29.

EXAMPLE 4

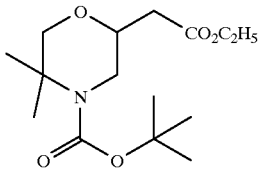

Dissolve 1 g of the product of Example 1 in ca. 10 mL of $CH_2Cl_2$ at room temperature. Add a solution of 1.2 g of di-t-butyl-dicarbonate, in ca. 3 mL of $CH_2Cl_2$. After about 0.5 h add a few drops of Hünig's Base and allow the reaction mixture to stand at room temperature overnight. Concentrate in vacuo to a residue, dissolve the residue in EtOAc and wash with brine Concentrate the organic layer to yield the title compound, m.p. 360–380C. Elemental Analysis for $C_{15}H_{27}NO_5$. Calcd. C, 59.78; H, 9.03; N, 4.65. Found, C, 60.00; H, 9.01; N, 5.37.

EXAMPLE 5

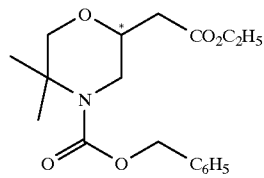

The racemic product of Example 3 is separated into its individual enantiomers by the following procedure. Inject 2 to 4 mL of a 10% solution of the product of Example 3 in 95:5 hexane:isopropanol onto a 50×500 mm Daicel Chiralcel OD® preparative HPLC column and elute with 95:5 hexane:isopropanol. Smaller injections give complete separation of the enantiomers, whereas larger injections give some mixed fractions between the two enantiomer peaks. The α-value for the separation is about 1.38 when measured using the identical solvent on a Daicel Chiralcel OD® analytical HPLC column. Combine pure fractions and evaporate the solvent to yield the two enantiomers, as follows: Enantiomer 1, Example 5A (eluting first from the column); Enantiomer 2, Example 5B (eluting second from the column):

EXAMPLE 6

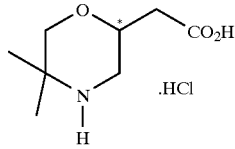

Step A:

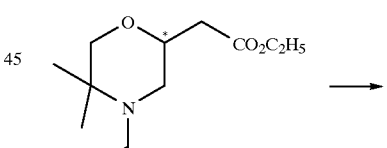

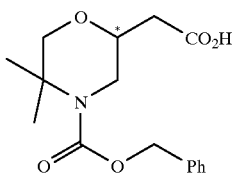

Dissolve 0.35 g of the product of Example 5A in 15 mL of a mixture of 1N NaOH (aqueous), MeOH, and THF (20:5:5), and stir the mixture at room temperature for 18 h. Add sufficient 1N HCl (aqueous) to bring the pH below 3, then dilute with EtOAc. Separate the organic layer, wash with 10 mL of water and then with 20 mL of brine. Dry the organic solution over $MgSO_4$, filter, and evaporate to yield 0.35 g of crude product.

Step B:

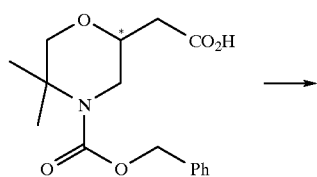

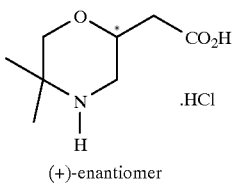

(+)-enantiomer

Dissolve the crude product of step A in 30 mL of methanol, add 100 mg of 10% Pd on C, and agitate the mixture under an atmosphere of $H_2$ for 18 h. Add 4 mL of 1N HCl (aqueous), filter and concentrate the filtrate in vacuo to yield 0.25 g of crude product. Purify by trituration with 1:9 acetone/EtOAc to give 0.08 g of the (+)-enantiomer of the title compound (Example 6A), mp 142–144° C. Analysis, calcd. for $C_8H_{15}NO_3 \cdot HCl$: C, 45.83; H, 7.69; N, 6.68; Found: C, 45.92; H, 7.58; N, 6.48. $[\alpha]_D = +17.30°$ (21.50° C., $H_2O$).

Using substantially the same two step procedure the product of Example 5B is converted to the (−)-enantiomer of the title compound:

EXAMPLE 6B

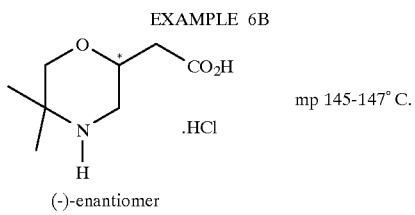

mp 145-147° C.

(−)-enantiomer

EXAMPLE 7

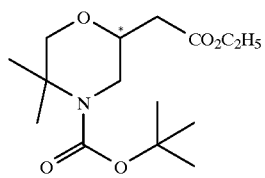

The racemic product of Example 4 can be separated into its individual enantiomers by the following procedure. Prepare a 10% solution of the product of Example 4 in 95:5 hexane: isopropanol. Inject 2.5 to 5.0 mL of this solution (containing from 250 to 500 mg of compound) onto a 50×500 mm Daicel Chiralcel OD® preparative HPLC column and elute with 99:1 hexane:isopropanol. The two enantiomers are completely separated under these conditions in just under one hour at a flow rate of 50 mL/min. The α-value for this separation is about 1.54. Combine the pure fractions and evaporate the solvent to yield the two enantiomers of the title compound as follows:

Example 7A, (+)-enantiomer (eluting first): m.p.=56°–58° C. Elemental Analysis: Calcd. for $C_{15}H_{27}NO_5$; C, 59.78; H, 9.03; N, 4.65. Found; C, 59.91; H, 8.78; N, 4.65. $[\alpha]_D+21.8°$ (23° C., MeOH)

Example 7B, (−)-enantiomer (eluting second): m.p. 56–58° C.; $[\alpha]_D$–20.6° (23° C., MeOH); Elemental Analysis: Calcd. for $C_{15}H_{27}NO_5$; C, 59.78; H, 9.03; N, 4.65. Found; C, 59.79; H, 8.73; N, 4.64.

EXAMPLE 8

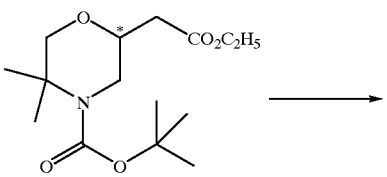

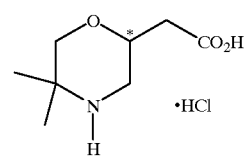

An alternative method of preparing the products of Example 6A and 6B is as follows. The product of Example 7B is hydrolyzed according to the procedure described in Example 6, Step A, to give the (−)-enantiomer, Example 6B, m.p.=154.5°–157° C. Elemental Analysis: Calcd. for $C_8H_{15}NO_3 \cdot HCl$; C, 45.83; H, 7.69; N, 6.68. Found; C, 45.76; H, 7.46; N, 6.61. $[\alpha]_D$–18.7° (23° C., $H_2O$)

In an analogous manner, the product of Example 7A is hydrolyzed to give the (+)-enantiomer, Example 6A, m.p. =154.5°–157° C. Elemental Analysis: Calcd. for $C_8H_{15}NO_3 \cdot HCl$; C, 45.83; H, 7.69; N, 6.68. Found; C, 45.71; H, 7.62; N, 6.61. $[\alpha]_D+16.5°$ (25° C., $H_2O$)

EXAMPLE 9

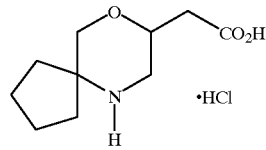

Heat a solution of 0.67 g of the product of Example 1 B in 25 mL of 1N HCl (aqueous) to reflux for 24 h. Cool to room temperature and treat with activated charcoal at 80° C. for 30 min. Filter and concentrate the filtrate in vacuo to give 0.75 g of crude product. Triturate with acetone to produce 0.56 g of the title compound, m.p. 186–188° C. Elemental Analysis, calcd. for $C_{10}H_{17}NO_3 \cdot HCl \cdot 0.3H_2O$, C, 49.81; H, 7.77; N, 5.80; Cl, 14.70. Found, C, 49.51; H, 7.47; N, 5.79; Cl, 14.86.

Using substantially the same procedure the product of Example 1A is converted to the following compound, Example 9A:

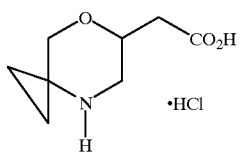

mp 188–190° C. Elemental Analysis, calcd. for $C_8H_{14}NO_3Cl·HCl·0.1H_2O$; C, 45.87; H, 6.83; N, 6.69; Cl, 16.93. Found; C, 45.68, 45.74; H, 6.71, 6.65; N, 6.78, 6.69; Cl, 16.99.

EXAMPLE 10

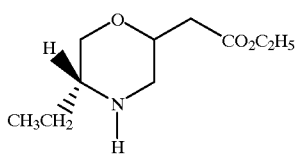

Dissolve 2.2 g of the product of Preparative Example 4 and 200 mg of DBU in 150 mL of toluene, and heat the solution at reflux temperature for 6 h. Concentrate in vacuo to a residue. Purify the residue by flash chromatography (silica gel, 97:3 $CH_2Cl_2$:MeOH/$NH_3$) to give the two diastereomers of the title compound:

EXAMPLE 10A
(first eluting diastereomer), 1.2 g

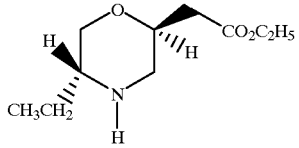

EXAMPLE 10B
(second eluting diastereomer), 0.13 g

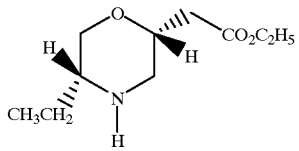

EXAMPLE 11

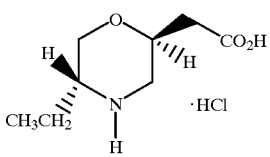

Heat a mixture of 1.2 g of the product of Example 10 A and 30 ML of 1N HCl (aqueous) at reflux for 18 h. Concentrate in vacuo and triturate the resulting residue with acetone to give the title compound. Purify by dissolving in 20 mL of 1N HCl, washing this solution with 3×10 mL of $CH_2Cl_2$, then treating the aqueous layer with activated charcoal. Filter, then concentrate the filtrate in vacuo to yield 0.45 g of partially purified title compound. A further purification by dissolution in 1N HCl, charcoal treatment, and evaporation, as before, gives 0.25 g of the purified title compound, m.p. 140–144° C.

EXAMPLE 12

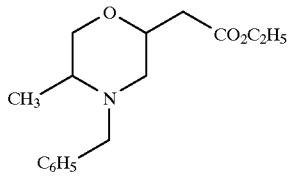

Heat a solution of 2.4 g of the product of Preparative Example 5 and 100 mg of DBU in 100 mL of toluene at reflux for 18 h. Concentrate in vacuo to a residue which is purified by flash chromatography (silica gel, 60:40 hexane/EtOAc) to yield 0.93 g of the cis-isomer (Example 13A) and 0.9 g of the trans-isomer (Example 13B) of the title compound. (The isomers are identified by $^1$H-NMR using a combination of coupling constants and NOE observations.)

EXAMPLE 12A

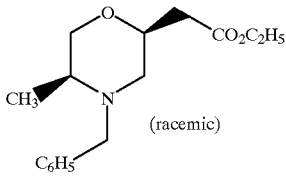

(racemic)

EXAMPLE 12B

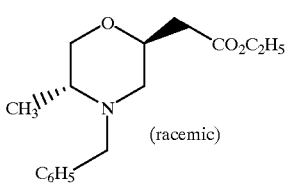

(racemic)

Using substantially the same procedure the product of Preparative Example 8 is converted to:

EXAMPLE 12C (racemic)
0.8 g

EXAMPLE 12D (racemic)
0.7 g and the product of Preparative Example 8A is converted to:

EXAMPLE 12E

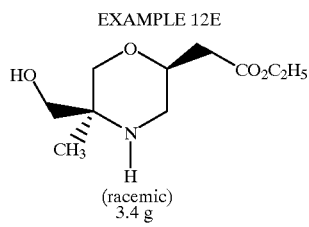

(racemic)
3.4 g

EXAMPLE 12F

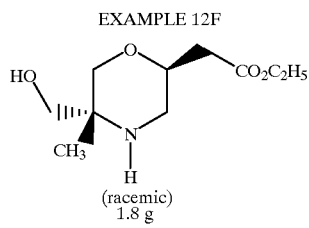

(racemic)
1.8 g

EXAMPLE 13

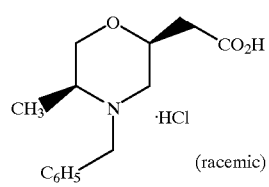

(racemic)

Heat a mixture of ca. 0.9 g of the product of Example 12A and 30 mL of 6N HCl (aqueous) at reflux for 18 h. Remove the solvent to yield 0.87 g of the crude product. Triturate with MeOH to give 0.7 g of the racemic title compound, mp 211–213° C.

Using substantially the same procedure: the product of Example 12B is converted to the trans-isomer of the title compound:

EXAMPLE 13A

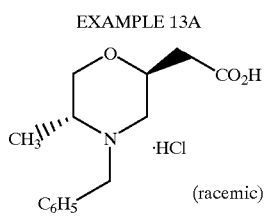

(racemic)

the product of Example 17B is converted to:

EXAMPLE 13B

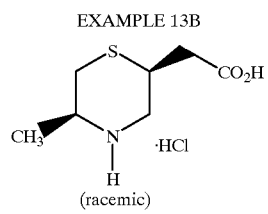

(racemic)

mp 134–137° C. Analysis, calcd. for $C_7H_{13}NO_2S \cdot HCl$: C, 39.71; H, 6.67; N, 6.62. Found, C, 39.88, 39.82; H, 6.76, 6.62; N, 6.49, 6.59;

the product of Example 17A is converted to:

EXAMPLE 13C

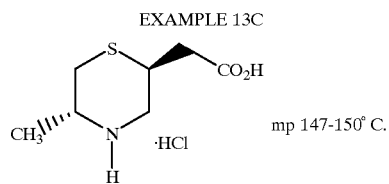

mp 147-150° C.

(racemic)

EXAMPLE 14

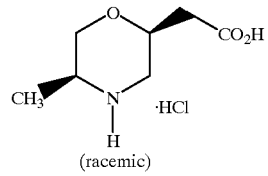

(racemic)

Add 100 mg of 10% Pd on C to 0.7 g of the product of Example 13 and 20 mL of 6N HCl. Hydrogenate the mixture under an atmosphere of $H_2$ at 60 psi for 18 h. Filter and concentrate the filtrate in vacuo to yield 0.45 g of the racemic title compound, m.p. 165–168° C.

Using substantially the same procedure the product of Example 13A is converted to the trans-isomer of the title compound:

EXAMPLE 14A

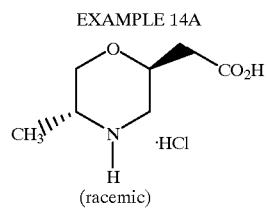

(racemic)

m.p. 219–221° C. Elemental Analysis: calcd. for $C_7H_{13}NO_3 \cdot HCl$: C, 42.97; H, 7.21; N, 7.16; Cl, 18.12. Found, C, 42.79; H, 7.36; N, 6.95; Cl, 18.19.

EXAMPLE 15

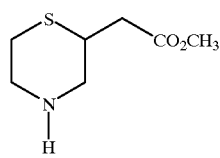

Heat a mixture of 4 g of the product of Preparative Example 6, 30 mL of 6N HCl and 2 mL of MeOH at reflux for 24 h. Concentrate in vacuo to a residue. Dissolve the residue in 100 mL of MeOH and treat with activated charcoal. Filter and concentrate the filtrate in vacua to give 3.5 g of the crude product. Suspend the product in 100 mL of EtOAc and let stand at 0° to 10° C. for 2 weeks. Filter, wash the solid with EtOAc, isopropanol, and then MeOH, and dry to yield 0.85 g of the title compound, mp 139–141° C., mass spectrum (CI) m/e 176 (M+1).

EXAMPLE 16

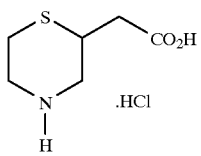

Stir a mixture of 60 mg of the product of Example 15 and 4 mL of 1N NaOH (aqueous) at room temperature for 18 h. Concentrate in vacuo and treat the residue with 4 mL of HCl in MeOH (concentrated). Filter and concentrate the filtrate in vacuo to a residue. Treat the residue with 2 mL of MeOH and 10 mL of $CH_2Cl_2$, filter, then concentrate the filtrate in vacuo to yield 50 mg of the title compound, mp 192–194° C. Elemental Analysis; Calcd. for $C_6H_{11}NO_2S \cdot HCl$; C, 36.45; H, 6.12; N, 7.09. Found, C, 36.17; H, 5.89; N, 6.81.

EXAMPLE 17

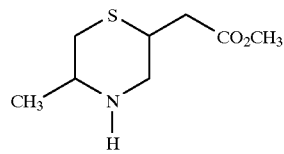

Combine 1 g of the product of Preparative Example 7 with 5 mL of 1N NaOH, 5 mL of water and 5 mL of MeOH, and stir at room temperature for 18 h. Quench the reaction mixture with 4 mL of 6N HCl and concentrate in vacuo to a residue. Treat the residue with MeOH, filter, and concentrate the filtrate in vacuo to yield 1.03 g of crude product. Treat the crude product with HCl/MeOH for 60 h, then evaporate the solvent to give the title compound.

The title compound (4 g) can be separated into its cis and trans isomers by preparative HPLC ($C_{18}$ reversed phase column, 20:80 $CH_3CN$/water) to give:

EXAMPLE 17A

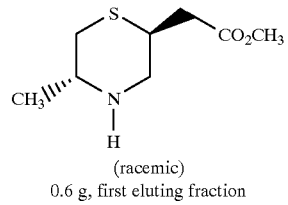

(racemic)
0.6 g, first eluting fraction

EXAMPLE 17B

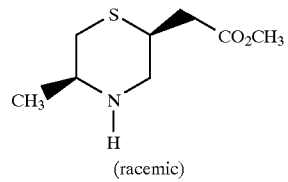

(racemic)
1.17 g, second eluting fraction

EXAMPLE 18

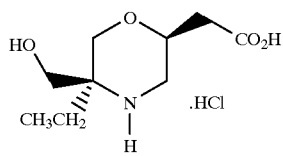

(racemic)

Dissolve 0.8 g of the product of Example 12C in 20 mL of 1N HCl and heat to reflux for 18 h. Concentrate in vacuo to yield 0.7 g of crude product. Triturate with acetone to produce 0.65 g of the title compound, mp 146–149° C. Analysis: C, 44.37; H, 7.58; N, 5.67. Calcd. for $C_9H_{17}NO_4 \cdot HCl \cdot 0.25H_2O$: C, 44.27; H, 7.64; N, 5.74.

EXAMPLE 19

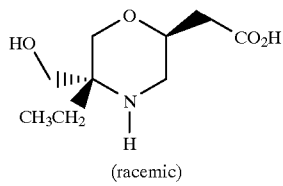

(racemic)

Dissolve 0.7 g of the product of Example 12D in 20 mL of 1 N HCl and heat at reflux for 18 h. Cool the reaction mixture and concentrate in vacuo to yield 0.69 g of crude product. Dissolve in EtOH and treat with an excess of propylene oxide at 0° C. for 18 h. Concentrate in vacuo to a residue and triturate the residue with 3×5 mL of ether. Dissolve the residue in 15 mL of water, add activated charcoal, heat for 5 min, filter, and concentrate in vacuo to yield 0.18 g of the title compound.

EXAMPLE 20

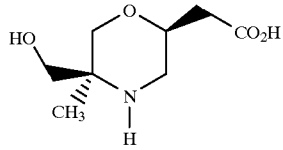

(racemic)

Dissolve 3.3 g of the product of Example 12E in 100 mL of 1N HCl (aqueous) and stir for 3 days at room temperature. Concentrate to a residue then triturate the residue with EtOAc to give 2.92 g of the title compound. Elemental analysis: calcd.. for $C_8H_{15}NO_4 \cdot HCl \cdot \frac{2}{3}H_2O$, C, 40.43; H, 7.35; N, 5.89, found, C, 40.30; H, 7.29; N, 5.81.

EXAMPLE 21

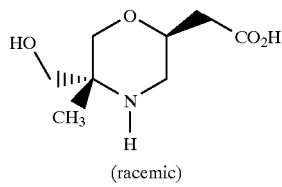

(racemic)

Dissolve 1.7 g of the product of Example 12F in 50 mL of 1N HCl and stir at room temperature for 3 days. Concentrate to a residue and chromatograph the residue (silica gel, 80:19:1 $CH_3CN/H_2O/1N$ HCl). Triturate the purified product with IPA to yield 0.74 g of the title compound. MS (Cl) m/e 190 (M+1)$^+$. Elemental analysis: calcd.. for $C_8H_{15}NO_4 \cdot HCl \cdot \frac{1}{2}H_2O$, C, 40.94; H, 7.30; N, 5.97, found, C, 40.59; H, 6.70; N, 5.89.

EXAMPLE 22

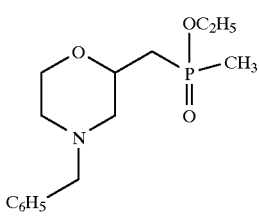

Combine 2.35 g of the product of Preparative Example 9, 3.3 g of N-benzyl-2-aminoethanol and 30 mL of toluene and heat the mixture at reflux for 18 h. Dilute the mixture with 100 mL of water and 50 mL of saturated $NaHCO_3$ (aqueous). Extract with 4×70 mL of EtOAc, combine the organic extracts and wash with brine. Dry the organic extracts over $MgSO_4$, filter and concentrate in vacuo to give 3.2 g of the crude product. Purify by flash chromatography (silica gel, 7% MeOH in $CH_2Cl_2$) to give 1.6 g of the title compound

EXAMPLE 23

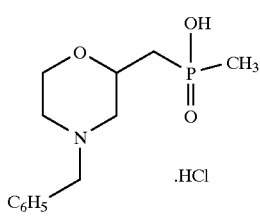

Combine 1.2 g of the product of Example 22 and 20 mL of concentrated HCl and heat the mixture at reflux for 18 h. Cool the mixture and concentrate in vacuo to give 1.08 g of crude product. Triturate with hot acetone to give 0.88 g of the title compound, m.p. 190°–192° C. FAB MS: m/e 270 (M+1)$^+$.

EXAMPLE 24

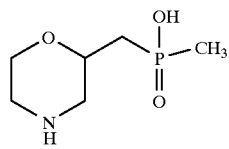

Combine 0.3 g of the product of Example 23, 20 mL of 1N HCl (aqueous) and 50 mg of 10% Pd/C and hydrogenate in a Parr shaker for 18 h. Filter and concentrate the filtrate in vacuo to give 0.21 g of crude product. Triturate with EtOAc and dry the solid under vacuum to give 0.2 g of the title compound. Elemental Analysis: calcd. for $C_6H_{14}NO_3P \cdot HCl \cdot H_2O$: C, 30.85; H, 7.33; N, 6.00; found: C, 30.90; H, 6.63; N, 5.76; C, 30.88; H, 6.64; N, 5.77.

EXAMPLE 25

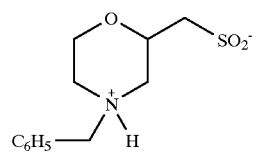

Combine 0.2 g of the product of Preparative Example 10 and 5 mL of glacial HOAc. Add 1.1 equivalents of TPP and warm to 75° C. When the starting compound is gone by TLC, cool to room temperature, concentrate in vacuo to a residue and purify by column chromatography (silica gel, $CH_2Cl_2$/30%–40% MeOH/3%–4% $NH_3$ (aq.)), to give the title compound.

EXAMPLE 26

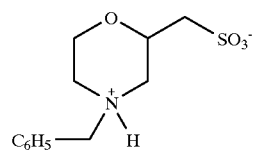

Step a:
Combine 0.25 g of the product of Preparation 10, 5 mL of $CH_2Cl_2$ and enough MeOH to form a solution. Add MCPBA and stir at room temperature. Concentrate in vacuo to a residue, then purify by column chromatography (silica gel, $CH_2Cl_2$/MeOH/$NH_3$ (aq.)), to give the sulfonate product.
Step b:
The product of step a is converted to the title compound via substantially the same procedure as described for Example 25.

EXAMPLE 27

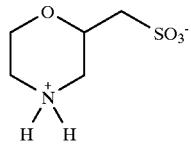

Combine 0.5 g of the title compound of Example 26, 10 mL of MeOH and 50 mg of 10% Pd/C. Agitate the mixture under H₂ atmosphere, then filter and concentrate the filtrate in vacua to a residue. Purify the residue by column chromatography to give the title compound.

Following substantially the same procedure, the title compound of Example 25 is converted to a compound of the formula

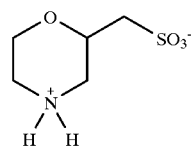

27A.

Using the in vitro assay methods described above, the following data were obtained:

| Example No. | Structure | Binding IC$_{50}$ or % inhibition (dose) | In Vitro IC$_{30}$ or % inhibition (dose) |
| --- | --- | --- | --- |
| 2 | (recemic) | 6 μM<br>96% (100 μM) | 1.5 μM<br>100% (300 μM) |
| 6A | (+)-enantiomer | 2 μM<br>94% (100 μM) | 1.1 μM<br>90% (30 μM) |
| 6B | (−)-enantiomer | >100 μM<br>8% (100 μM) | 42%<br>(300 μM) |
| 9 | 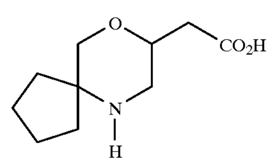 | 10 μM<br>95% (100 μM) | 97%<br>(300 μM) |
| 9A | 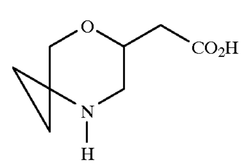 | 37 ± 12 μM<br>76% (100 μM) | |
| 11 | 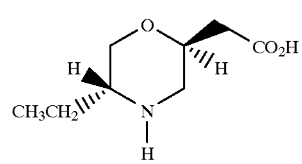 | 14 μM<br>82% (100 μM) | 95%<br>(300 μM) |

-continued

| Example No. | Structure | Binding IC$_{50}$ or % inhibition (dose) | In Vitro IC$_{30}$ or % inhibition (dose) |
|---|---|---|---|
| 13B | (2S,5R)-5-methyl-thiomorpholine-2-CH$_2$CO$_2$H (racemic) | 60 μM<br>55% (100 μM) | |
| 13C | 5-methyl-thiomorpholine-2-CH$_2$CO$_2$H (racemic) | 20 μM<br>81% (100 μM) | 88%<br>(300 μM) |
| 14 | 5-methyl-morpholine-2-CH$_2$CO$_2$H (racemic) | 20 μM<br>74% (100 μM) | 95%<br>(300 μM) |
| 14A | 5-methyl-morpholine-2-CH$_2$CO$_2$H (racemic) | 30 μM<br>63% (100 μM) | 75%<br>(300 μM) |
| 16 | thiomorpholine-2-CH$_2$CO$_2$H | >100<br>44% (100 μM) | — |
| 18 | 5-(hydroxymethyl)-5-ethyl-morpholine-2-CH$_2$CO$_2$H (racemic) | 100 ± 40 μM<br>50% (100 μM) | |
| 19 | 5-(hydroxymethyl)-5-ethyl-morpholine-2-CH$_2$CO$_2$H (racemic) | 19 ± 10 μM<br>90% (100 μM) | 99%<br>(300 μM) |

-continued

| Example No. | Structure | Binding IC$_{50}$ or % inhibition (dose) | In Vitro IC$_{30}$ or % inhibition (dose) |
|---|---|---|---|
| — | morpholine-2-CH$_2$CO$_2$H (NH) | 50 μM<br>59% (100 μM) | 46%<br>(300 μM) |
| — | 6-CH$_3$-thiomorpholine-2-CH$_2$CO$_2$H | >100 μM<br>21% (100 μM) | — |
| — | (2R,5S)-5-C$_2$H$_5$-morpholine-2-CH$_2$CO$_2$H | 100 μM<br>50% (100 μM) | — |
| — | (2R,5R)-5-C$_2$H$_5$-morpholine-2-CH$_2$CO$_2$H | >100 μM<br>17% (100 μM) | — |
| 23 | 4-C$_6$H$_5$-morpholine-2-CH$_2$-P(O)(OH)CH$_3$ | >100 μM<br>31% (100 μM) | — |
| 24 | morpholine-2-CH$_2$-P(O)(OH)CH$_3$ | 6 μM<br>100% (100 μM) | 98%<br>(300 μM) |
| — | 5,5-diMe-morpholine-2-CH$_2$-P(O)(OH)CH$_3$ | 2 μM<br>100% (100 μM) | 1.9 μM |

-continued

| Example No. | Structure | Binding IC$_{50}$ or % inhibition (dose) | In Vitro IC$_{30}$ or % inhibition (dose) |
|---|---|---|---|
| 20 | (structure: morpholine with HO-CH2, CH3, CO2H) (racemic) | 3.8 μM | 24% (30 μM) |
| 21 | (structure: morpholine with HO-CH2, CH3, CO2H) (racemic) | 0.85 μM | — |
| — | (structure: spiro morpholine with P(=O)(CH3)(OH)) | 3 μM | 3.3 μM |

Using the in vivo test methods described above, the following results (Tables A, B, C, D & E) were obtained using the compound of Example 6A as the test compound:

TABLE A

Prevention of seizure in rats induced by GBL

Test Compound — SWD[1] duration (sec) at specified time (min) after treatment with 100 mg/kg GBL (ip)

| Dose | 20 | 40 | 60 | 80 | 100 | 120 |
|---|---|---|---|---|---|---|
| control | 990 | 1150 | 500 | 300 | 75 | 5 |
| 0.75 mg/kg | 970 | 1150 | 500 | 280 | 50 | 0 |
| 1.5 mg/kg | 560 | 540 | 0 | 0 | 0 | 0 |
| 3.0 mg/kg | 0 | 0 | 0 | 0 | 0 | 0 |

[1]Values are given as spiked wave discharge (SWD) duration in seconds.

TABLE B

Prevention of seizure in rats induced by PTZ

Test Compound — SWD[1] duration (sec) at specified time (min) after treatment with 20 mg/kg GBL (ip)

| Dose | 20 | 40 | 60 | 80 | 100 | 120 |
|---|---|---|---|---|---|---|
| control | 285 | 260 | 150 | 70 | 20 | 5 |
| 0.18 mg/kg | 250 | 235 | 140 | 60 | 15 | 0 |
| 0.375 mg/kg | 150 | 140 | 55 | 25 | 0 | 0 |
| 0.75 mg/kg | 90 | 70 | 45 | 0 | 0 | 0 |
| 1.5 mg/kg | 0 | 0 | 0 | 0 | 0 | 0 |

[1]Values are given as spiked wave discharge (SWD) duration in seconds.

TABLE C

Prevention of seizure in lethargic (lh/lh) mice

| Dose of Test Compound (ip) | Seizures (% vehicle) in 120 min. |
|---|---|
| vehicle alone | 100% |
| 1.0 mg/kg | 85% |
| 3.0 mg/kg | 60% |
| 10 mg/kg | 15% |
| 30 mg/kg | 5% |

TABLE D

Inhibition of Respiratory Depressant Effect of Baclofen[a]

| Dose (mg/kg) | % Inhibition[2] (sc) | % Inhibition[2] (oral)[1] | % inhibition[2] (ip) |
|---|---|---|---|
| 0.3 | 27 ± 6(6) | — | 39 ± 10(9) |
| 1.0 | 66 ± 7(9) | 36 ± 13(6) | 32 ± 7(15) |
| 3.0 | 97 ± 25(6) | 51 ± 13(12) | 59 ± 7(18) |
| 10 | 99 ± 11(12) | 68 ± 13(12) | 100 ± 9(18) |
| 30 | — | 78 ± 29(11) | — |
| ED$_{50}$ (mg/kg) | 0.63 | 3.0 | 1.9 |

[a]Baclofen alone inhibited ventilation 44–60%.
[1]Test compound was given orally 60 min prior to baclofen.
[2]Results are given as the mean ± SEM. Number in parentheses is the number of animals tested.

TABLE E

Reversal of the Respiratory Depressant
Effect of Baclofen via icv Administration[a]

| Treatment[1] | No. of Animals tested | % Inhibition[2] |
|---|---|---|
| 50 μg in 10 μl of vehicle | 5 | 99 ± 23 |

[a]Baclofen plus vehicle inhibited ventilation 82 ± 5%.
[1]Given 5 min before measurement of ventilation.
[2]Mean ± SEM The following are examples of pharmaceutical dosage forms which contain a compound of the invention. As used therein, the term "active compound" is used to designate a compound of the formula

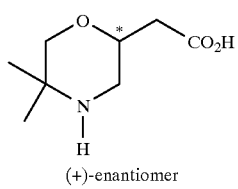

(+)-enantiomer

The scope of the invention in its pharmaceutical composition aspect is not to be limited by the examples provided, since any other compound of formula I can be substituted into the pharmaceutical composition examples.

Pharmaceutical Dosage Form Examples

EXAMPLE A

Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

EXAMPLE B

Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
| | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A compound of the formula I

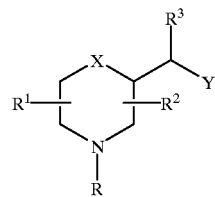

wherein:

X is O or S;

Y represents —$CO_2H$, —$CO_2R^6$, C—(O)$NHR^7$, —$SO_3H$, —$SO_2H$, —$SO_3R^6$, —$SO_2NHR^7$, —C(O)—N(OH)—$R^8$, or a group of the formula

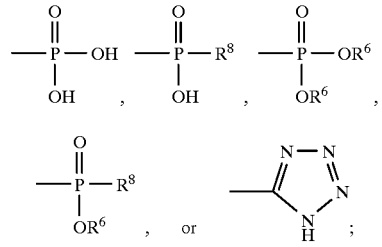

R is selected from the group consisting of H, $C_1$–$C_8$ alkyl, $C_1$–$C_8$ alkanoyl, $C_1$–$C_8$ alkoxycarbonyl, $C_3$–$C_8$ cycloalkyl, $C_3$–$C_8$ cycloalkyl($C_1$–$C_8$)alkyl, Ar—($C_1$–$C_8$)alkyl and Ar—$CH_2$—O—C(O)—;

Ar represents phenyl optionally substituted by 1 to 3 substituents selected from $C_1$–$C_6$ alkyl, halogeno, —CN, —$NO_2$, —$CF_3$, —OH, —$OR^6$ and —$OCF_3$;

$R^1$ is selected from the group consisting of $C_1$–$C_8$ alkyl and hydroxy($C_1$–$C_8$)alkyl; and $R^1$ also represents H where:

(a) R is H and $R^7$ is $C_1$–$C_6$ alkyl or

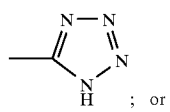 ; or (b) X is S; or
(c) Y is —$SO_3H$, —$SO_2H$, —$SO_3R^6$, —$SO_2NHR^7$, or a group of the formula

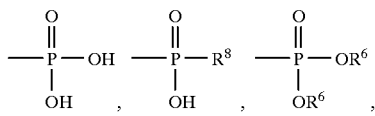

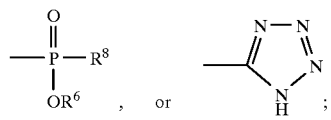 ;

$R^2$ is selected from the group consisting of H, $C_1$–$C_8$ alkyl and hydroxy($C_1$–$C_8$)alkyl; or
where $R^1$ and $R^2$ are both attached at the 5-position of the heterocyclic ring: $R^1$ and $R^2$ together with the carbon atom to which they are attached may also form a 3–8 membered carbocyclic spiro ring, which ring may be optionally substituted by an —OH group;
$R^3$ is H, $C_1$–$C_8$ alkyl or hydroxy($C_1$–$C_8$)alkyl;
$R^6$ is $C_1$–$C_6$ alkyl;
$R^7$ is H, $C_1$–$C_6$ alkyl or

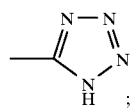 ;

$R^8$ is H, $C_1$–$C_8$ alkyl, $C_3$–$C_8$ cycloalkyl, $C_3$–$C_8$ cycloalkyl($C_1$–$C_8$)alkyl, Ar or Ar—($C_1$–$C_8$)alkyl;
or a pharmaceutically acceptable addition salt or solvate thereof.

2. A compound of claim 1 having the structural formula

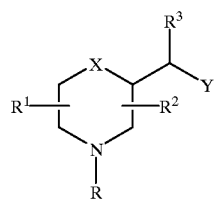

wherein

| R | $R^1$ | $R^2$ | $R^3$ | X | Y |
|---|---|---|---|---|---|
| H | —$CH_3$ | —$CH_3$ | H | O | —$CO_2C_2H_5$ |
| H | —$CH_2CH_2$— | | H | O | —$CO_2C_2H_5$ |
| H | —$(CH_2)_4$— | | H | O | —$CO_2C_2H_5$ |
| H | —$CH_3$ | —$CH_3$ | H | O | —$CO_2H$ |
| $C_6H_5CH_2OC(O)$— | —$CH_3$ | —$CH_3$ | H | O | —$CO_2C_2H_5$ |
| $(CH_3)_3COC(O)$— | —$CH_3$ | —$CH_3$ | H | O | —$CO_2C_2H_5$ |
| $C_6H_5CH_2OC(O)$— | —$CH_3$ | —$CH_3$ | H | O | —$CO_2H$ |

-continued

| R | $R^1$ | $R^2$ | $R^3$ | X | Y |
|---|---|---|---|---|---|
| H | —$(CH_2)_4$— | | H | O | —$CO_2H$ |
| H | —$CH_2CH_2$— | | H | O | —$CO_2H$ |
| H | —$CH_2CH_3$ | H | H | O | —$CO_2C_2H_5$ |
| H | —$CH_2CH_3$ | H | H | O | —$CO_2C_2H_5$ |
| $C_6H_5CH_2$— | —$CH_3$ (2,5-cis) | H | H | O | —$CO_2C_2H_5$ |
| $C_6H_5CH_2$— | —$CH_3$ (2,5-trans) | H | H | O | —$CO_2C_2H_5$ |
| H | —$CH_2CH_3$ | —$CH_2OH$ | H | O | —$CO_2C_2H_5$ |
| H | —$CH_2CH_3$ | —$CH_2OH$ | H | O | —$CO_2H$ |
| $C_6H_5CH_2$— | —$CH_3$ (2,5-cis) | H | H | O | —$CO_2H$ |
| $C_6H_5CH_2$— | —$CH_3$ (2,5-trans) | H | H | O | —$CO_2H$ |
| H | —$CH_3$ (2,5-cis) | H | H | S | —$CO_2H$ |
| H | —$CH_3$ (2,5-trans) | H | H | S | —$CO_2H$ |
| H | —$CH_3$ (2,5-cis) | H | H | O | —$CO_2H$ |
| H | —$CH_3$ (2,5-cis) | H | H | O | —$CO_2H$ |
| H | —$CH_3$ (2,5-trans) | H | H | O | —$CO_2H$ |
| H | —$CH_3$ (2,5-cis) | H | H | S | —$CO_2CH_3$ |
| H | —$CH_3$ (2,5-trans) | H | H | S | —$CO_2CH_3$ |
| H | H | H | $CH_3$ | S | —$CO_2H$ |
| H | —$CH_2CH_3$ (2,5-cis) | H | H | O | —$CO_2H$ |
| H | —$CH_2CH_3$ (2,5-trans) | H | H | O | —$CO_2H$ |
| $C_6H_5CH_2$— | H | H | H | O | $-\overset{\overset{\displaystyle O}{\|}}{\underset{\underset{\displaystyle OH}{\|}}{P}}-CH_3$ |
| H | —$(CH_2)_4$— | | H | O | $-\overset{\overset{\displaystyle O}{\|}}{\underset{\underset{\displaystyle OH}{\|}}{P}}-CH_3$ |
| H | $CH_3$ | $CH_3$ | H | O | $-\overset{\overset{\displaystyle O}{\|}}{\underset{\underset{\displaystyle OH}{\|}}{P}}-CH_3$ |
| H | $CH_3$ | —$CH_2OH$ | H | O | —$CO_2H$ |
| H | H | H | H | O | $-\overset{\overset{\displaystyle O}{\|}}{\underset{\underset{\displaystyle OH}{\|}}{P}}-CH_3$ |
| H | $CH_3$ | —$CH_2OH$ | H | O | —$CO_2C_2H_5$. |

3. A compound of claim 1 wherein $R^1$ is selected from the group consisting of $C_1$–$C_8$ alkyl and hydroxy($C_1$–$C_8$)alkyl; and
$R^1$ also represents H where:
(a) X is S; or (b) Y is —SO$_3$H, —SO$_2$H, —SO$_3$R$^6$, —SO$_2$NHR$^7$, or a group of the formula

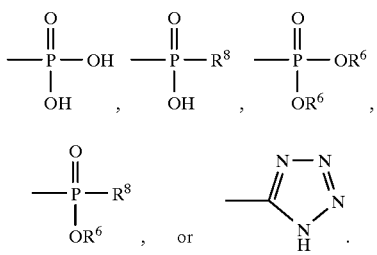

4. A compound of claim 3 wherein R$^3$ is H and Y is —CO$_2$H, —CO$_2$R$^6$, —C(O)NHR$^7$, or —C(O)—N(OH)—R$^8$.

5. A compound of claim 4 wherein R$^3$ is H, and R$^1$ and R$^2$ are independently selected from H, —CH$_3$, —C$_2$H$_5$ or —CH$_2$OH.

6. A compound of claim 4 wherein R$^3$ is H, and R$^1$ and R2, together with the carbon atom to which they are attached, comprise a 3–8 membered carbocyclic spiro ring, which ring is optionally substituted by an —OH group.

7. A pharmaceutical composition comprising an effective amount of a compound of claim 1 in combination with a pharmaceutically acceptable carrier.

8. A compound of having the structural formula

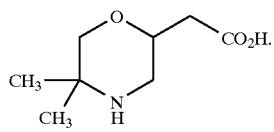

9. A compound of claim 8 which is a single enantiomer, the hydrochloride salt of which has a (+) optical rotation as measured in methanolic or aqueous solution at room temperature.

10. A compound selected from the group consisting of:

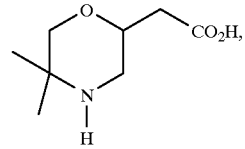

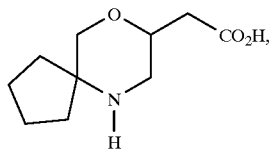

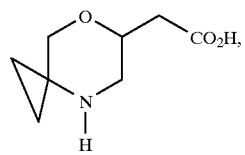

-continued

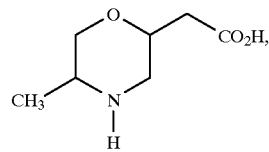

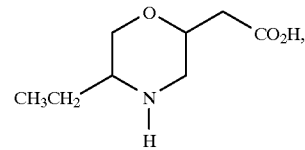

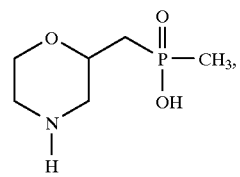

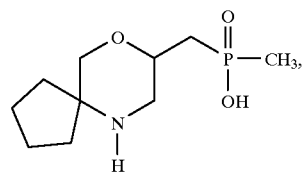

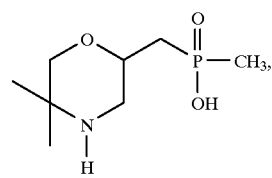

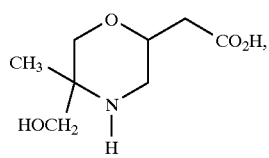

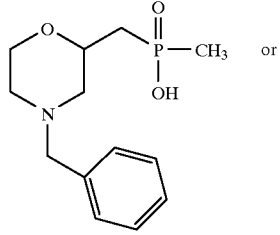

or

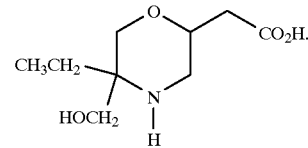

* * * * *